United States Patent
Fillatti et al.

(10) Patent No.: US 9,920,326 B1
(45) Date of Patent: Mar. 20, 2018

(54) METHODS AND COMPOSITIONS FOR INCREASING INVERTASE ACTIVITY IN PLANTS

(75) Inventors: Joanne J. Fillatti, Davis, CA (US); Byron Froman, Davis, CA (US); Andrew Mroczka, Sacramento, CA (US); Gregory John Peel, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 331 days.

(21) Appl. No.: 13/619,876

(22) Filed: Sep. 14, 2012

Related U.S. Application Data

(60) Provisional application No. 61/534,863, filed on Sep. 14, 2011.

(51) Int. Cl.
*C12N 15/113* (2010.01)
*C12N 15/82* (2006.01)

(52) U.S. Cl.
CPC ..... *C12N 15/8218* (2013.01); *C12N 15/8266* (2013.01); *C12N 15/8282* (2013.01)

(58) Field of Classification Search
None
See application file for complete search history.

(56) References Cited

U.S. PATENT DOCUMENTS

| | | |
|---|---|---|
| 3,687,808 A | 8/1972 | De et al. |
| 3,850,752 A | 11/1974 | Schuurs et al. |
| 3,935,074 A | 1/1976 | Rubenstein et al. |
| 4,023,525 A | 5/1977 | Weber |
| 4,079,696 A | 3/1978 | Weber |
| 4,476,301 A | 10/1984 | Imbach et al. |
| 4,535,060 A | 8/1985 | Comai |
| 4,581,847 A | 4/1986 | Hibberd et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,971,908 A | 11/1990 | Kishore et al. |
| 5,004,863 A | 4/1991 | Umbeck |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,562 A | 11/1993 | Matteucci |
| 5,264,564 A | 11/1993 | Matteucci |
| 5,304,732 A | 4/1994 | Anderson et al. |
| 5,310,667 A | 5/1994 | Eichholtz et al. |
| 5,312,910 A | 5/1994 | Kishore et al. |
| 5,331,107 A | 7/1994 | Anderson et al. |
| 5,378,824 A | 1/1995 | Bedbrook et al. |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,463,174 A | 10/1995 | Moloney et al. |
| 5,463,175 A | 10/1995 | Barry et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |

(Continued)

FOREIGN PATENT DOCUMENTS

| | | |
|---|---|---|
| CN | 101914540 A | 12/2010 |
| EP | 1416049 A1 | 5/2004 |

(Continued)

OTHER PUBLICATIONS

Jin et al, 2009, The Plant Cell, 21:2072-2089.*
Fuglevand et al, 1998, GenBank Accession No. AJ010943.*
Momentive Performance Materials, Inc., 2003, "Silwet L-77 Spray Adjuvant for agricultural applications".*
Liu et al, 2000, Pest Manag., Sci., 56:861-866).*
Gao et al, 2008, Mol. Pharmaceutics, 6:651-658.*
Kim et al, 2009, Plant Cell Rep., 28:1159-1167.*
Kirkwood, Ralph C., "Use and Mode of Action of Adjuvants for Herbicides: A Review of some Current Work", Pesticide Science, 1993, pp. 93-102, vol. 38.
Kusaba et al., "Low glutelin content1: A Dominant Mutation That Supresses the Glutelin Multigene Family via RNA Silencing in Rice", The Plant Cell, 2003, pp. 1455-1467, vol. 15.
First Examination Report issued for New Zealand Application No. 601784 dated Apr. 23, 2013.
Unnamalai et al., "Cationic oligopeptide-mediated delivery of dsRNA for post-transcriptional gene silencing in plant cells", FEBS Letters, 2004, pp. 307-310, vol. 566.

(Continued)

*Primary Examiner* — Jason Deveau Rosen
(74) *Attorney, Agent, or Firm* — Thompson Coburn LLP; Charles P. Romano; Amanda J. Carmany-Rampey

(57) ABSTRACT

The present invention provides novel compositions for use to enhance crop performance. Specifically, the present invention provides for increased invertase activity, increased sugar content and/or delayed senescence plants. The present invention also provides for combinations of compositions and methods that increase invertase activity, increase sugar content and/or delay senescence in plants.

7 Claims, 1 Drawing Sheet

(56) References Cited

U.S. PATENT DOCUMENTS

| | | | |
|---|---|---|---|
| 5,541,307 A | 7/1996 | Cook et al. |
| 5,550,111 A | 8/1996 | Suhadolnik et al. |
| 5,550,318 A | 8/1996 | Adams et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,866,775 A | 2/1999 | Eichholtz et al. |
| 5,874,265 A | 2/1999 | Adams et al. |
| 5,876,739 A | 3/1999 | Turnblad et al. |
| 5,879,903 A | 3/1999 | Strauch et al. |
| 5,891,246 A | 4/1999 | Lund |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,225,105 B1 | 5/2001 | Sathasivan et al. |
| 6,225,114 B1 | 5/2001 | Eichholtz et al. |
| 6,245,968 B1 | 6/2001 | Boudec et al. |
| 6,248,876 B1 | 6/2001 | Barry et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,453,609 B1 | 9/2002 | Soll et al. |
| 6,506,559 B1 | 1/2003 | Fire et al. |
| 6,582,516 B1 | 6/2003 | Carlson |
| 6,644,341 B1 | 11/2003 | Chemo et al. |
| 6,768,044 B1 | 7/2004 | Boudec et al. |
| 6,870,075 B1 * | 3/2005 | Beetham et al. ............. 800/278 |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,405,347 B2 | 7/2008 | Hammer et al. |
| 7,406,981 B2 | 8/2008 | Hemo et al. |
| 7,485,777 B2 | 2/2009 | Nakajima et al. |
| 7,525,013 B2 | 4/2009 | Hildebrand et al. |
| 7,622,301 B2 | 11/2009 | Ren et al. |
| 7,671,254 B2 | 3/2010 | Tranel et al. |
| 7,714,188 B2 | 5/2010 | Castle et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,143,480 B2 | 3/2012 | Axtell et al. |
| 8,642,505 B2 | 2/2014 | Kohn |
| 9,121,022 B2 | 9/2015 | Sammons et al. |
| 9,422,557 B2 | 8/2016 | Ader et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0167537 A1 | 9/2003 | Jiang |
| 2003/0235916 A1 | 12/2003 | Monahan et al. |
| 2004/0053289 A1 | 3/2004 | Christian et al. |
| 2004/0055041 A1 | 3/2004 | Labate et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0244075 A1 | 12/2004 | Cai et al. |
| 2005/0026290 A1 * | 2/2005 | Ciardi ................ C12N 15/8249 435/468 |
| 2005/0239728 A1 * | 10/2005 | Pachuk ................ C12N 15/111 514/44 A |
| 2006/0021087 A1 | 1/2006 | Baum et al. |
| 2006/0111241 A1 | 5/2006 | Gerwick et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |

(56) References Cited

U.S. PATENT DOCUMENTS

| | | |
|---|---|---|
| 2009/0018016 A1 | 1/2009 | Duck et al. |
| 2009/0098614 A1 | 4/2009 | Zamore et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0188005 A1 | 7/2009 | Boukharov et al. |
| 2009/0205079 A1 | 8/2009 | Kumar et al. |
| 2009/0293148 A1 | 11/2009 | Ren et al. |
| 2009/0307803 A1 | 12/2009 | Baum et al. |
| 2010/0005551 A1 | 1/2010 | Roberts et al. |
| 2010/0068172 A1 | 3/2010 | Van De Craen |
| 2010/0071088 A1 | 3/2010 | Sela et al. |
| 2010/0100988 A1 | 4/2010 | Tranel et al. |
| 2010/0154083 A1 | 6/2010 | Ross et al. |
| 2010/0247578 A1 | 9/2010 | Salama |
| 2011/0035836 A1 | 2/2011 | Eudes et al. |
| 2011/0098180 A1 | 4/2011 | Michel et al. |
| 2011/0105327 A1 | 5/2011 | Nelson |
| 2011/0126310 A1 | 5/2011 | Feng et al. |
| 2011/0126311 A1 | 5/2011 | Velcheva et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0296555 A1 | 12/2011 | Ivashuta et al. |
| 2011/0296556 A1* | 12/2011 | Sammons et al. ............ 800/298 |
| 2012/0036594 A1 | 2/2012 | Cardoza et al. |
| 2012/0137387 A1 | 5/2012 | Baum et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0067618 A1 | 3/2013 | Ader et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0215656 A1 | 7/2014 | Crawford et al. |
| 2014/0230090 A1 | 8/2014 | Avniel et al. |
| 2014/0274712 A1 | 9/2014 | Finnessy et al. |
| 2014/0283211 A1 | 9/2014 | Crawford et al. |
| 2014/0296503 A1 | 10/2014 | Avniel et al. |
| 2015/0247153 A1 | 9/2015 | Fillatti et al. |

FOREIGN PATENT DOCUMENTS

| | | |
|---|---|---|
| EP | 2 530 159 A1 | 12/2012 |
| JP | 2006343473 A | 12/2006 |
| WO | 89/11789 A1 | 12/1989 |
| WO | 96/05721 A1 | 2/1996 |
| WO | 96/33270 A1 | 10/1996 |
| WO | 96/38567 A2 | 12/1996 |
| WO | 96/40964 A2 | 12/1996 |
| WO | 99/24585 A1 | 5/1999 |
| WO | 99/32619 A1 | 7/1999 |
| WO | 99/61631 A1 | 12/1999 |
| WO | 99/67367 A1 | 12/1999 |
| WO | 00/32757 A2 | 6/2000 |
| WO | 00/44914 A1 | 8/2000 |
| WO | 02/14472 A2 | 2/2002 |
| WO | 03/106636 A2 | 12/2003 |
| WO | 2004/005485 A2 | 1/2004 |
| WO | 2004/009761 A2 | 1/2004 |
| WO | 2004/022771 A2 | 3/2004 |
| WO | 2004/074443 A2 | 9/2004 |
| WO | 2005/003362 A2 | 1/2005 |
| WO | 2005/007860 | 1/2005 |
| WO | 2005/107437 A2 | 11/2005 |
| WO | 2005/110068 A2 | 11/2005 |
| WO | 2006/074400 A2 | 7/2006 |
| WO | 2006/138638 A1 | 12/2006 |
| WO | 2007/007316 A1 | 1/2007 |
| WO | 2007/035650 A2 | 3/2007 |
| WO | 2007/039454 A1 | 4/2007 |
| WO | 2007/051462 A2 | 5/2007 |
| WO | 2007/070389 A2 | 6/2007 |
| WO | 2007/074405 A2 | 7/2007 |
| WO | 2007/080126 A2 | 7/2007 |
| WO | 2007/080127 A2 | 7/2007 |
| WO | 2008/007100 A2 | 1/2008 |
| WO | 2008/063203 A2 | 5/2008 |
| WO | 2008/148223 A1 | 12/2008 |
| WO | 2009/046384 A1 | 4/2009 |
| WO | 2009/116558 A1 | 9/2009 |
| WO | 2009/125401 A2 | 10/2009 |
| WO | 2010/078912 A1 | 7/2010 |
| WO | 2010/104217 A1 | 9/2010 |
| WO | 2010/108611 A1 | 9/2010 |
| WO | 2010/112826 A2 | 10/2010 |
| WO | 2010/116122 A2 | 10/2010 |
| WO | 2010/119906 A1 | 10/2010 |
| WO | 2010/130970 A1 | 11/2010 |
| WO | 2011/001434 A1 | 1/2011 |
| WO | 2011/003776 A2 | 1/2011 |
| WO | 2011/067745 A2 | 6/2011 |
| WO | 2011/080674 A2 | 7/2011 |
| WO | 2011/112570 A1 | 9/2011 |
| WO | 2011/132127 A1 | 10/2011 |
| WO | 2012/001626 A1 | 1/2012 |
| WO | 2012/056401 A1 | 5/2012 |
| WO | 2012/092580 A2 | 7/2012 |
| WO | 2013/010691 A1 | 1/2013 |
| WO | 2013/025670 A1 | 2/2013 |
| WO | 2013/039990 A1 | 3/2013 |
| WO | 2013/040005 A1 | 3/2013 |
| WO | 2013/040021 A1 | 3/2013 |
| WO | 2013/040033 A1 | 3/2013 |
| WO | 2013/040049 A1 | 3/2013 |
| WO | 2013/040057 A1 | 3/2013 |
| WO | 2013/040116 A9 | 3/2013 |
| WO | 2013/040117 A1 | 3/2013 |
| WO | 2013/040117 A9 | 6/2013 |
| WO | 2013/175480 A1 | 11/2013 |
| WO | 2014/106837 A2 | 7/2014 |
| WO | 2014/106838 A2 | 7/2014 |
| WO | 2014/151255 A1 | 9/2014 |
| WO | 2014/164761 A1 | 10/2014 |
| WO | 2014/164797 A1 | 10/2014 |
| WO | 2015/010026 A2 | 1/2015 |

OTHER PUBLICATIONS

Al-Kaff et al., "Plants rendered herbicide-susceptible by cauliflower mosaic virus-elicited suppression of a 35S promoter-regulated transgene", Nature Biotechnology, 2000, pp. 995-999, vol. 18.

Gao et al., "Nonviral Methods for siRNA Delivery", Molecular Pharmaceutics, 2008, pp. 651-658, vol. 6 No. 3.

Busch et al., "RNAi for discovery of novel crop protection products", Pflanzenschutz-Nachrichten Bayer, 2005, pp. 34-50, vol. 58 No. 1.

Roberts, Michael R., "Fast-track applications: The potential for direct delivery of proteins and nucleic acids to plant cells for the discovery of gene function", Plant Methods, 2005, vol. 1 No. 12.

Basu et al., "Weed genomics: new tools to understand weed biology", TRENDS in Plant Science, 2004, pp. 391-398, vol. 9 No. 8.

(56) References Cited

OTHER PUBLICATIONS

Tenllado et al., "Double-Stranded RNA-Mediated Interference with Plant Virus Infection", Journal of Virology, 2001, pp. 12288-12297, vol. 75 No. 24.
Bart et al., "A novel system for gene silencing using siRNAs in rice leaf and stem-derived protoplasts", Plant Methods, 2006, vol. 2 No. 13.
Fraley et al., "Liposome-mediated delivery of tobacco mosaic virus RNA into tobacco protoplasts: A sensitive assay for monitoring liposome-protoplast interactions", Proceedings of the National Academy of Sciences, 1982, pp. 1859-1863, vol. 79.
Tang et al., "Efficient delivery of small interfering RNA to plant cells by a nanosecond pulsed laser-induced stress wave for post-transcriptional gene silencing", Plant Science, 2006, pp. 375-381, vol. 171.
Waterhouse et al., "Exploring Plant Genomes by RNA-Induced Gene Silencing", Nature Reviews, Genetics, 2003, pp. 29-38, vol. 4.
Tang et al., "Antisense Repression of Vacuolar and Cell Wall Invertase in Transgenic Carrot Alters Early Plant Development and Sucrose Partitioning", The Plant Cell, 1999, pp. 177-189, vol. 11.
Roitsch et al., "Extracellular invertase: key metabolic enzyme and PR protein", Journal of Experimental Botany, 2003, pp. 513-524, vol. 54 No. 382.
Balibrea Lara et al., "Extracellular Invertase is an Essential Component of Cytokinin-Mediated Delay of Senescence", The Plant Cell, 2004, pp. 1276-1287, vol. 16.
Gan et al., "Inhibition of Leaf Senescence by Autoregulated Production of Cytokinin." Science, 1995, pp. 1986-1988, vol. 270.
Kambiranda et al., "Relationship Between Acid Invertase Activity and Sugar Content in Grape Species", Journal of Food Biochemistry, 2011, pp. 1646-1652, vol. 35.
Jin et al., "Posttranslational Elevation of Cell Wall Invertase Activity by Silencing Its Inhibitor in Tomato Delays Leaf Senescence and Increases Seed Weight and Fruit Hexose Level" The Plant Cell, 2009, pp. 2072-2089, vol. 21.
Hajirezaei, et al., "Impact of elevated cytosolic and apoplastic invertase activity on carbon metabolism during potato tuber development." Journal of Experimental Botany, 2000 pp. 439-445, vol. 51.
Liu et al., "Identification and Application of a Rice Senescence-Associated Promoter", Plant Physiology, 2010, pp. 1239-1249, vol. 153.
Mounet et al., "Gene and Metabolite Regulatory Network Analysis of Early Developing Fruit Tissues Highlights New Candidate Genes for the Control of Tomato Fruit Composition and Development", Plant Physiology, 2009, pp. 1505-1528, vol. 149.
Nookaraju et al., "Molecular approaches for enhancing sweetness in fruits and vegetables." Scientia Horticulturae, 2010, pp. 1-15, vol. 127.
Robson et al., "Leaf senescence is delayed in maize expressing the Agrobacterium IPT gene under the control of a novel maize senescence-enhanced promoter", Plant Biotechnology Journal, 2004, pp. 101-112, vol. 2.
Roitsch et al., "Function and regulation of plant invertases: sweet sensations", Trends in Plant Science, 2004, pp. 606-613, vol. 9 No. 12.
Ruan et al., "Suppression of Sucrose Synthase Gene Expression Represses Cotton Fiber Cell Initiation, Elongation, and Seed Development", The Plant Cell, 2003, pp. 952-964, vol. 15.
Tomlinson et al., "Evidence that the hexose-to-sucrose ratio does not control the switch to storage product accumulation in oilseeds: analysis of tobacco seed development and effects of overexpressing apoplastic invertase", Journal of Experimental Botany, 2004, pp. 2291-2303, vol. 55 No. 406.
Jones-Rhoades et al., "MicroRNAs and Their Regulatory Roles in Plants", Annual Review of Plant Biology, 2006, pp. 19-53, vol. 57.
Reynolds et al., "Rational siRNA Design for RNA Interference", Nature Biotechnology, Mar. 2004, pp. 326-330, vol. 22 No. 3.

Pei et al., "On the Art of Identifying Effective and Specific siRNAs", Nature Methods, Sep. 2006, pp. 670-676, vol. 3 No. 9.
Zhang et al., "Agrobacterium-mediated Transformation of Arabidopsis thaliana Using the Floral Dip Method", Nature Protocols, 2006, pp. 1-6, vol. 1 No. 2.
Brodersen et al., "The Diversity of RNA Silencing Pathways in Plants", Trends in Genetics, May 2006, pp. 268-280, vol. 22 No. 5.
Tomari et al., "Perspective: Machines for RNAi", Genes & Development, 2005, pp. 517-529, vol. 19.
Vaucheret, Hervé, "Post-transcriptional Small RNA Pathways in Plants: Mechanisms and Regulations", Genes & Development, 2006, pp. 759-771, vol. 20.
Meins, Jr. et al., "RNA Silencing Systems and Their Relevance to Plant Development", Annual Review of Cell and Developmental Biology, 2005, pp. 297-318, vol. 21.
Hamilton et al., "Two Classes of Short Interfering RNA in RNA Silencing", The European Molecular Biology Organization Journal, 2002, pp. 4671-4679, vol. 21, No. 17.
Du et al., "A Systematic Analysis of the Silencing Effects of an Active siRNA at All Single-nucleotide Mismatched Target Sites", Nucleic Acids Research, 2005, pp. 1671-1677, vol. 33 No. 5.
Concise Descriptions of Relevance filed by a third party on Nov. 29, 2012 in U.S. Appl. No. 13/042,856.
Hunter, Wayne B., "RNA Interference Strategies to Suppress Psyllids", International Plant and Animal Genome XIX, Jan. 15-19, 2011.
International Search Report and Written Opinion for PCT/US2011/27528 dated May 10, 2011.
Gan et al., "Bacterially Expressed dsRNA Protects Maize Against SCMV Infection", Plant Cell Reports, published online Aug. 24, 2010.
Tenllado et al., "Crude Extracts of Bacterially Expressed dsRNA can be used to Protect Plants Against Virus Infection" BMC Biotechnology, 2003, pp. 1-11, vol. 3 No. 3.
Sun et al., "Antisense Oligodeoxynucleotide Inhibition as a Potent Strategy in Plant Biology: Identification of SUSIBA2 as a Transcriptional Activator in Plant Sugar Signalling", The Plant Journal, 2005, pp. 128-138, vol. 44.
Baulcombe, David, "RNA Silencing and Heritable Epigenetic Effects in Tomato and Arabidopsis", Abstract 13th Annual Fall Symposium, Plant Genomes to Phenomes, Donald Danforth Plant Science Center, Sep. 28-30, 2011.
Himber et al., "Transitivity-dependent and -independent Cell-to-Cell Movement of RNA Silencing", The European Molecular Biology Organization Journal, 2003, pp. 4523-4533, vol. 22 No. 17.
Ryabov et al., "Cell-to-Cell, but Not Long-Distance, Spread of RNA Silencing That is Induced in Individual Epidermal Cells", Journal of Virology, Mar. 2004, pp. 3149-3154, vol. 78 No. 6.
COST Action FA0806 progress report, "Plant virus control employing RNA-based vaccines: A novel non-transgenic strategy", 2010.
European Cooperation in the field of Scientific and Technical Research, Memorandum of Understanding for COST Action FA0806, 2008.
Devgen, "The mini-Monsanto", KBC Securities, 2006.
Clough et al., "Floral dip: a simplified method for Agrobacterium-mediated transformation of Arabidopsis thaliana", The Plant Journal, 1998, pp. 735-743, vol. 16 No. 6.
Nowak et al., "A new and efficient method for inhibition of RNA viruses by DNA interference", The FEBS Journal, 2009, pp. 4372-4380, vol. 276.
Klahre et al., "High molecular weight RNAs and small interfering RNAs induce systemic posttranscriptional gene silencing in plants", PNAS, 2002, pp. 11981-11986, vol. 99 No. 18.
Liu et al., "Comparative study on the interaction of DNA with three different kinds of surfactants and the formation of multilayer films", Bioelectrochemistry, 2007, pp. 301-307, vol. 70.
Melnyk et al., "Intercellular and systemic movement of RNA silencing signals", The EMBO Journal, 2011, pp. 3553-3563, vol. 30.
Reddy et al., "Organosilicone Adjuvants Increased the Efficacy of Glyphosate for Control of Weeds in Citrus (*Citrus* spp.)", HortScience, 1992, pp. 1003-1005, vol. 27 No. 9.

(56) References Cited

OTHER PUBLICATIONS

Zhu et al., "Ingested RNA interference for managing the populations of the Colorado potato beetle, Leptinotarsa decemlineata", Pest Management Science, 2010, pp. 175-182, vol. 67.
Maas et al., "Mechanism and optimized conditions for PEG mediated DNA transfection into plant protoplasts", Plant Cell Reports, 1989, pp. 148-151, vol. 8.
Wardell, William L., "Floral Activity in Solutions of Deoxyribonucleic Acid Extracted from Tobacco Stems", Plant Physiology, 1976, pp. 855-861, vol. 57.
Wardell, William L., "Floral Induction of Vegetative Plants Supplied a Purified Fraction of Deoxyribonucleic Acid from Stems of Flowering Plants", Plant Physiology, 1977, pp. 885-891, vol. 60.
Hewezi et al., "Local infiltration of high- and low-molecular-weight RNA from silenced sunflower (Helianthus annuus L.) plants triggers post-transcriptional gene silencing in non-silenced plants", Plant Biotechnology Journal, 2005, pp. 81-89, vol. 3.
Zhao et al., "Phyllotreta striolata (Coleoptera: Chrysomelidae): Arginine kinase cloning and RNAi-based pest control", European Journal of Entomology, 2008, pp. 815-822, vol. 105.
Hannon, Gregory J., "RNA interference", Nature, 2002, pp. 244-251, vol. 418.
Tenllado, et al., "RNA interference as a new biotechnological tool for the control of virus diseases in plants", Virus Research, 2004, pp. 85-96, vol. 102.
Silwet L-77 Spray Adjuvant for agricultural applications, product description from Momentive Performance Materials, Inc., 2003.
Gong et al., "Silencing of Rieske iron-sulfur protein using chemically synthesised siRNA as a potential biopesticide against Plutella xylostella", Pest Management Science, 2011, pp. 514-520, vol. 67.
Dunoyer et al., "Small RNA Duplexes Function as Mobile Silencing Signals Between Plant Cells", Science, 2010, pp. 912-916, vol. 328.
Molnar et al., "Small Silencing RNAs in Plants are Mobile and Direct Epigenetic Modification in Recipient Cells", Science, 2010, pp. 872-875, vol. 328.
Sun et al., "Sweet delivery—sugar translocators as ports of entry for antisense oligodeoxynucleotides in plant cells", The Plant Journal, 2007, pp. 1192-1198, vol. 52.
Voinnet et al., "Systemic Spread of Sequence-Specific Transgene RNA Degradation in Plants is Initiated by Localized Introduction of Ectopic Promoterless DNA", Cell, 1998, pp. 177-187, vol. 95.
An et al., "Transient RNAi Induction against Endogenous Genes in Arabidopsis Protoplasts Using in Vitro-Prepared Double-Stranded RNA", Bioscience Biotechnology and Biochemistry, 2005, pp. 415-418, vol. 69 No. 2.
YouTube video by General Electric Company "Silwet Surfactants," screen shots taken on Jan. 11, 2012 of video of www.youtube_com/watch?v=WBw7nXMqHk8 (uploaded Jul. 13, 2009).
Artymovich, Katherine A., "Using RNA interference to increase crop yield and decrease pest damage", MMG 445 Basic Biotechnology, 2009, pp. 7-12, vol. 5.
Li et al., "The FAST technique: a simplified Agrobacterium-based transformation method for transient gene expression analysis in seedlings of Arabidopsis and other plant species", Plant Methods, 2009, vol. 5 No. 6.
Paungfoo-Lonhienne et al., "DNA is Taken up by Root Hairs and Pollen, and Stimulates Root and Pollen Tube Growth", Plant Physiology, 2010, pp. 799-805, vol. 153.
Paungfoo-Lonhienne et al., "DNA uptake by Arabidopsis induces changes in the expression of CLE peptides which control root morphology", Plant Signaling & Behavior, 2010, pp. 1112-1114, vol. 5 No. 9.
International Preliminary Report on Patentability for PCT/US2011/027528 dated Sep. 11, 2012.
Gaines et al., "Gene amplification confers glyphosate resistance in Amaranthus palmeri", PNAS, 2010, pp. 1029-1034, vol. 107 No. 3.
Thomas et al., "Size Constraints for Targeting Post-Transcriptional Gene Silencing and for RNA-Directed Methylation in Nicotiana Benthamiana using a Potato Virus X Vector", The Plant Journal, 2001, pp. 417-425, vol. 25 No. 4.

Chen et al., "Transfection and Expression of Plasmid DNA in Plant Cells by an Arginine-Rich Intracellular Delivery Peptide without Protoplast Preparation", FEBS Letters 581, 2007, pp. 1891-1897.
Kim et al., "Optimization of Conditions for Transient Agrobacterium-Mediated Gene Expression Assays in Arabidopsis", Plant Cell Reports, 2009, pp. 1159-1167, vol. 28.
Schweizer et al., "Double-stranded RNA interferes with gene function at the single-cell level in cereals", The Plant Journal, 2000, pp. 895-903, vol. 24, No. 6.
Office Action for U.S. Appl. 13/619,980 dated Apr. 7, 2016.
"Agricultural Chemical Usage 2006 Vegetables Summary", Agricultural Statistics Board, Jul. 2007, pp. 1-372.
Kirkwood, "Herbicides and Plants", Botanical Journal of Scotland, Jan. 1, 1993, pp. 447-462, vol. 46 Issue 3.
Kusaba, "RNA interference in crop plants," Curr Opin Biotechnol, 15(2):139-143 (2004).
Li et al., "The FAST technique: a simplified Agrobacterium-based transformation method for transient gene expression analysis in seedlings of Arabidopsis and other plant species," Plant Methods, 5(6):1-15 (2009).
Orbovic et al., "Foliar-Applied Surfactants and Urea Temporarily Reduce Carbon Assimilation of Grapefruit Leaves", Journal of the American Society for Horticultural Science, 2001, pp. 486-490, vol. 126.
Showalter, "Structure and Function of Plant Cell Wall Proteins", The Plant Cell, Jan. 1993, pp. 9-23, vol. 5.
Stevens et al., "New Formulation Technology—Sil Wet® Organosilicone Surfactants Have Physical and Physiological Properties Which Enhance the Performance of Sprays", Proceedings of the 9th Australian Weeds conference, pp. 327-331 (1990).
Stevens, "Organosilicone Surfactants as Adjuvants for Agrochemicals", Journal of Pesticide Science, 1993, pp. 103-122, vol. 38.
Stock et al., "Possible Mechanisms for Surfactant-Induced Foliar Uptake of Agrochemicals", Pesticide Science, 1993, pp. 165-177, vol. 38.
Zhang et al., "Cationic Lipids and Polymers Mediated Vectors for Delivery of siRNA", Journal of Controlled Release, Oct. 18, 2007, pp. 1-10, vol. 123 Issue. 1.
Gelvin, "Agrobacterium-Mediated Plant Transformation: The Biology Behind the "Gene-Jockeying" Tool", Microbiology and Molecular Biology Reviews, Mar. 2003, p. 16-37, vol. 67 No. 1.
Somerville et al., "Plant Functional Genomics" Science, 285:380-383 (1999).
Wamasooriya et al., "Using transgenic modulation of protein synthesis and accumulation to probe protein signaling networks in Arabidopsis thaliana" Plant Signaling & Behavior, 6(9):1312-1321 (2011).
Zhai et al., "Establishing RNA Interference as a Reverse-Genetic Approach for Gene Functional Analysis in Protoplasts" Plant Physiology, 149:642-652 (2009).
AGRIOS, Plant Pathology (Second Edition), 2:466-470 (1978).
Alarcón-Reverte et al., "Resistance to ACCase-inhibiting herbicides in the weed Lolium multiflorum," Comm. Appl. Biol. Sci., 73(4):899-902 (2008).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
Anonymous, "Do Monsanto Have the Next Big Thing?" Australian Herbicide Resistance Initiative (AHRI), retreived on Jan. 19, 2015, XP007922963.
Anonymous, "A handbook for high-level expression and purification of 6xHis-tagged proteins," The QIAexpressionist, (2003).
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (Solanum melongena L) resistant to Colorado Potato Beetle (Leptinotarsa decemlineata Say)," (1997) Theor. Appl. Genet., 95:329-334 (1997).

(56) References Cited

OTHER PUBLICATIONS

Australian Patent Examination report No. 1 dated Nov. 11, 2013, in Australian Application No. 2011224570.
Axtell et al., "A Two-Hit Trigger for siRNA Biogenesis in Plants," Cell, 127:565?577 (2006).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occurring Broad-Spectrum Powdery Mildew Resistance in a Central American Tomato Accession is Caused by Loss of Mb Function," MPMI, 2I(1):30-39 (2008).
Baneriee et al., "Efficient production of transgenic potato (S. tuberosum L. ssp. andigena) plants via Agrobacterium tumefaciens-mediated transformation," Plant Sci., 170:732 738 (2006).
Bayer et al., "Programmable ligand-controlled riboregulators of eukaryotic gene expression," Nature Biotechnol, 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(Diabrotica virgifera virgifera LeConte)," PLoS One 7(10):e47534 (2012).
Bolter et al., "A chloroplastic inner envelope membrane protease is essential for plant development," FEBS Letters, 580:789-794 (2006).
Bourgeois et al., "Field and Producer Survey of Accase Resistant Wild Oat in Manitoba," Canadian Journal of Plant Science, 709-7 15 (1997).
Breaker et al., "A DNA enzyme with Mg2+-dependent RNA phosphoesterase activity," Chemistry and Biology, 2:655-660 (1995).
Brugiére et al., "Glutamine Synthetase in the Phloem Plays a Major Role in Controlling Proline Production," The Plant Cell, 11:1995-2011(1999).
Busi et al., "Gene Flow Increases the Initial Frequency of Herbicide Resistance Alleles in Unselected Lolium Rigidum Populations", Agriculture, Ecosystems and Environments, 2011, pp. 403-409, vol. 142.
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Cellular Internalization of Fluorescent Proteins via Arginine-Rich Intracellular Delivery Peptide in Plant Cells", Plant Cell Physiology, 2005, pp. 482-488, vol. 46.
Chee et al., "Transformation of Soybean (Glycine max) by Infecting Germinating Seeds with Agrobacterium tumefaciens," Plant Physiol., 91:1212-1218 (1989).
Chen et al., "In Vivo Analysis of the Role of atTic20 in Protein Import into Chloroplasts," The Plant Cell, 14:641-654 (2002).
Cheng et al., "Production of fertile transgenic peanut (Arachis hypogaea L.) plants using Agrobacterium tumefaciens," Plant Cell Reports, 15:653-657 (1996).

Chi et al., "The Function of RH22, a DEAD RNA Helicase, in the Biogenesis of the 50S Ribosomal Subunits of Arabidopsis Chloroplasts," Plant Physiology, 158:693-707 (2012).
Chinese Office Action dated Aug. 28, 2013 in Chinese Application No. 201180012795.2.
Chupp et al., "Chapter 8: White Rust," Vegetable Diseases and Their Control, The Ronald Press Company, New York, pp. 267-269 (1960).
Colbourne et al., "The Ecoresponsive Genome of Daphnia pulex," Science, 331(6017):555-561 (2011).
Colombian Office Action dated Aug. 2, 2013 in Application No. 12 152898.
Colombian Office Action dated Feb. 21, 2014 in Application No. 12 152898.
Communication pursuant to Article 94(3) EPC dated Jun. 26, 2015, as received in European Patent Application No. 11 753 916.3.
Dalmay et al., "An RNA-Depenedent RNA Polymerase Gene in Arabidopsis is Required for Posttranscriptional Gene Silencing Mediated by a Transgene but not by a Virus," Cell, 101:543-553 (2000).
Datebase EMBL CBIB Daphnia—XP-002732239 (2011).
Davidson et al., "Engineering regulatory RNAs," Trends in Biotechnology, 23(3):109-112 (2005).
De Block, et al. "Engineering herbicide resistance in plants by expression of a detoxifying enzyme," EMBO J. 6 (9):2513-2519 (1987).
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," The EMBO Journal, 7(5):1299-1305 (1988).
Diallo et al., "Long Endogenous dsRNAs can Induce Complete Gene Silencing in Mammalian Cells and Primary Cultures," Oligonucleotides, 13:381-392 (2003).
Ellington et al., "In vitro selection of RNA molecules that bind specific ligands," Nature, 346:818-822 (1990).
Emery et al., "Radial Patterning of Arabidopsis Shoots by Class III HD-ZIP and KANADI Genes," Current Biology, 13:1768-1774 (2003).
Eurasian Office Action dated Feb. 24, 2014, in Application No. 201201264.
European Supplemental Search Report dated Oct. 8, 2013 in Application No. 11753916.3.
Extended European Search Report dated Jun. 29, 2015, in European Patent Application No. 12831494.5.
Farooq et al., "Rice seed priming," IPRN, 30(2):45-48 (2005).
Final Office Action dated Nov. 7, 2013, in U.S. Appl. No. 13/042,856.
Fire et al., "Potent and specific genetic interference by double-stranded RNA in Caenorhabditis elegans," Nature, 391:806-811 (1998).
First Examination Report dated Jul. 28, 2014, in New Zealand Patent Application No. 627060.
First Office Action dated May 27, 2015, in Chinese Patent Application No. 201280054179.8.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270 (30):18147-18149 (1995).
Fukuhara et al., "The wide distribution of endomaviruses, large double-stranded RNA replicons with plasmid-like properties," Archives of Virology, 151:995-1002 (2006).
Further Examination Report issued in New Zealand Patent Application No. 601784 dated May 16, 2014.
Ge et al., "Rapid vacuolar sequestration: the horseweed glyphosate resistance mechanism," Pest Management Sci., 66:345-348 (2010).
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006)

(56) References Cited

OTHER PUBLICATIONS

[Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. GI:186478573, published Jan. 22, 2014.
GenEmbl FJ861243, published Feb. 3, 2010.
Gressel et al., "A Strategy to Provide Long-Term Control of Weedy Rice While Mitigating Herbicide Resistance Transgene Flow, and Its Potential Use for Other Crops with Related Weeds", Pest Management Science, 2009, pp. 723-731, vol. 65.
Gutensohn et al., "Functional analysis of the two Arabidopsis homologues of Toc34, a component of the chloroplast protein import apparatus," The Plant Journal, 23(6):771-783 (2000).
Haigh, "The Priming of Seeds: Investigation into a method of priming large quantities of seeds using salt solutions," Thesis submitted to Macquarie University (1983).
Han et al., "Molecular Basis for the Recognition of Primary microRNAs by the Drosha-DGCR8 Complex," Cell, 125 (5):887-901 (2006).
Hardegree, "Drying and storage effects on germination of primed grass seeds," Journal of Range Management, 47 (3):196-199 (1994).
Herman et al., "A three-component dicamba O-demethylase from Pseudomonas maltophilia, strain DI-6: gene isolation, characterization, and heterologous expression," J. Biol. Chem., 280: 24759-24767 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (Solanum tuberosum L cv Desiree) Plants," Plant Physiol., 107(2):469-477 (1995).
Hsieh et al., "A library of siRNA duplexes targeting the phosphoinositide 3-kinase pathway: determinants of gene silencing for usein cell-based screens," Nucleic Acids Res., 32(3):893-901 (2004).
Huesken et al., "Design of a genome-wide siRNA library using an artificial neural network," Nature Biotechnology, 23 (8): 995-1001 (2005).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2014, in International Application No. PCT/IL13/50447.
International Search Report and the Written Opinion dated Feb. 25, 2013, in International Application No. PCT/US12/54883.
International Search Report and the Written Opinion dated Feb. 27, 2013, in International Application No. PCT/US12/54814.
International Search Report and the Written Opinion dated Feb. 27, 2013, in International Application No. PCT/US12/54842.
International Search Report and the Written Opinion dated Feb. 27, 2013, in International Application No. PCT/US12/54862.
International Search Report and the Written Opinion dated Feb. 27, 2013, in International Application No. PCT/US12/54894.
International Search Report and the Written Opinion dated Feb. 27, 2013, in International Application No. PCT/US12/54974.
International Search Report and the Written Opinion dated Feb. 27, 2013, in International Application No. PCT/US12/54980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Jul. 8, 2015 in International Application No. PCT/US2015/011408.
International Search Report and Written Opinion dated Mar. 26, 2015, in International Application No. PCT/US2014/069353.
International Search Report dated Mar. 12, 2013 in International Application No. PCT/US 12/54789.
Isaacs et al., "Engineered riboregulators enable post-transcriptional control of gene expression," Nature Biotechnology, 22(7):841-847 (2004).
Khan et al., "Matriconditioning of Vegetable Seeds to Improve Stand Establishment in Early Field Plantings," .1 Amer. Soc. Hon. Sci., 1 17(1):41-47 (1992).
Ji et al., "Regulation of small RNA stability: methylation and beyond," Cell Research, 22:624-636 (2012).
Jofre-Garfias el al., "Agrobacerium—Mediated Transformation of Amaranthus Hypochondriacus: Light- And Tissue-Specific Expression of a Pea Chlorophyll A/B—Binding Protein Promoter," Plant Cell Reports, 16:847-852 (1997).
Josse et al., "A DELLA in Disguise: SPATULA Restrains the Growth of the Developing Arabidopsis Seedling," Plant Cell, 23:1337-1351 (2011).
Kam et al., "Nanotube Molecular Transporters:? Internalization of Carbon Nanotube?Protein Conjugates into Mammalian Cells," J. Am. Chem. Soc., 126(22):6850-6851 (2004).
Katoh et al., "Specific residues at every third position of siRNA shape its efficient RNAi activity," Nucleic Acids Res., 35 (4): e27 (2007).
Kertbundit et al., "In vivo random β-glucuronidase gene fusions in Arabidopsis thaliana," Proc. Natl. Acad. Sci. U S A., 88:5212-5216 (1991).
Khachigian, "DNAzymes: Cutting a path to a new class of therapeutics," Cuff Opin Mol Ther 4(2):119-121 (2002).
Khodakovskaya et al., "Carbon Nanotubes are Able to Penetrate Plant Seed Coat and Dramatically Affect Seed Germination and Plant Growth," ACS Nano, 3(10):3221-3227 (2009).
Kim et al., "Synthetic dsRNA Dicer substrates enhance RNAi potency and efficacy," Nature Biotechnology, 23 (2):222-226 (2005).
Kronenwett et al., "Oligodeoxyribonucleotide Uptake in Primary Human Hematopoietic Cells is Enhanced by Cationic Lipids and Depends on the Hematopoietic Cell Subset," Blood, 91(3):852-862 (1998).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Leopold et al., "Chapter 4: Moisture as a Regulator of Physiological Reaction in Seeds," Seed Moisture, CSSA Special Publication No. 14, pp. 51-69 (1989).
Li et al., "Establishment of a highly efficient transformation system for pepper (Capsicum annuum L.)," Plant Cell Reports, 21: 785-788 (2003).
Liu et al., "Carbon Nanotubes as Molecular Transporters for Walled Plant Cells," Nano Letters, 9(3):1007-1010 (2009).

(56) References Cited

OTHER PUBLICATIONS

Liu et al., "DNAzyme-mediated recovery of small recombinant RNAs from a 5S rRNA-derived chimera expressed in *Escherichia coli*," BMC Biotechnology, 10:85 (2010).
Llave et al., "Endogenous and Silencing-Associated Small RNAs in Plants," The Plant Cell, 14:1605-1619 (2002).
Lu et al., "OligoWalk: an online siRNA design tool utilizing hybridization thermodynamics," Nucleic Acids Research, 36: W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
Mackenzie et al., "Transgenic Nicotiana Debneyii Expressing Viral Coat Protein are Resistant to Potato Virus S Infection," Journal of General Virology, 71:2167-2170 (1990).
Maher III et al., "Inhibition of DNA binding proteins by oligonucleotide-directed triple helix formation," Science, 245 (4919):725-730 (1989).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," Transgenic Research, 5:313-323 (1996).
Matveeva et al., "Prediction of antisense oligonucleotide efficacy by in vitro methods," Nature Biotechnology, 16:1374-1375 (1998).
Meinke, et al., "Identifying essential genes in Arabidopsis thaliana," Trends Plant Sci., 13(9):483-491 (2008).
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (1994).
Misawa et al., "Functional expression of the Erwinia uredovora carotenoid biosynthesis gene crtI in transgenic plants showing an increase of ?-carotene biosynthesis activity and resistance to the bleaching herbicide norilurazon," The Plant Journal, 4(5):833-840 (1993).
Miura et al., "The Balance between Protein Synthesis and Degradation in Chloroplasts Determined Leaf Variegation in Arabidopsis yellow variegated Mutants," The Plant Cell, 19:1313-1328 (2007).
Miolina et al., "Inhibition of Protoporphyrinogen Oxidase Expression in Arabidopsis Causes a Lesion-Mimic Phenotype That Induces Systemic Acquired Resistance," The Plant Journal, 1 7(6):667-678 (1999).
Molnar et al., "Plant Virus-Derived Small Interfering RNAs Originate Predominantly from Highly Structured Single-Stranded Viral RNAs," Journal of Virology, 79(12):7812-7818 (2005).
Moriyama et al., "Double-stranded RNA in rice: a novel RNA replicon in plants," Molecular & General Genetics, 248 (3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23 (8):1002-1007 (2005).
Moser et al., "Sequence—Specific Cleavage of Double Helical DNA by Triple Helix Formation," Science, 238:645-646 (1987).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated May 15, 2015, in U.S. Appl. No. 14/608,951.
Non-Final Office Action dated May 22, 2015, in U.S. Appl. No. 13/612,985.
Office Action dated Feb. 17, 2014, in Mexican Patent Application No. MX/a/2012/010479.
Office Action for UA Application No. 201211548 dated Jul. 23, 2015.
Office Action dated Jan. 6, 2015, in Japanese Patent Application No. 2012-557165.
Office Action dated Nov. 19, 2014, in Eurasian Patent Application No. 201201264128.
Office Action dated Nov. 3, 2014, in Chinese Patent Application No. 201180012795.2.
Office Action dated Oct. 8, 2014, in Mexican Patent Application MX/A/2012/010479.
Paddison et al., "Stable suppression of gene expression by RNAi in mammalian cells," Proc. Natl Acad. Sci. USA, 99 (3):1443-1448 (2002).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Peretz et al., "A Universal Expression/Silencing Vector in Plants," Plant Physiology, 145:1251-1263 (2007).
Pomprom et al., "Glutamine synthetase mutation conferring target-site-based resistance to glufosinate in soybean cell selections," Pest Manag Sci, 2009; 65(2):216-222 (2009).
Pratt et al., "*Amaranthus rudisa A. tuberculatus*, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Qiwei,"Progress in DNA interference," Progress in Veterinary Medicine, 30(1):71-75 (2009).
Rajur et al., "Covalent Protein-Oligonucleotide Conjugates for Efficient Delivery of Antisense Molecules," Bioconjug Chem., 8:935-940 (1997).
Reddy et al., "Aminomethylphosphonic Acid Accumulation in Plant Species Treated with Glyphosate," J. Agric. Food Chem., 56(6):2125-2130 (2008).
Reither et al., "Specificity of DNA triple helix formation analyzed by a FRET assay," BMC Biochemistry, 3:27 (2002).
Riggins et al., "Characterization of De Nova Transcriptome for Waterhemp (*Amaranthus tuberculalus* ) Using Gs-Flx 454 Pyrosequeneing and Its Application for Studies of Herbicide Target-Site Genes," Pest Manag. Sci., 66:1042-1052 (2010).
Rose et al., "Functional Polarity is Introduced by Dicer Processing of Short Substrate RNAs," Nucleic Acids Research, 33(13):4140-4156 (2005).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schwab et al., "RNA silencing amplification in plants: Size matters," PNAS, 107(34):14945-14946 (2010).

(56) References Cited

OTHER PUBLICATIONS

Schwember et al., "Drying Rates following Priming Affect Temperature Sensitivity of Germination and Longevity of Lettuce Seeds," HortScience, 40(3):778-781 (2005).
Second Chinese Office Action issued in Chinese Patent Application No. 201180012795.2, dated Jun. 10, 2014.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. *Aggregatum*) and carrot (*Daucus carota*)," Journal of Agricultural Technology, 7(3):857-867 (2011).
Senthil-Kumar et al., "A Systematic Study to Determine the Extent of Gene Silencing in Nicotiana Benthamiana and Other Solanaccac Species When Heterologous Gene Sequences Are Used for Virus-Induced Gene Silencing", New Phylologist, 176:782-791 (2007).
Sharma et al., "A simple and efficient Agrobacterium-mediated procedure for transformation of tomato," J. Biosci., 34 (3):423 433 (2009).
Sijen et al., "On the Role of RNA Amplification in dsRNA-Triggered Gene Silencing," Cell, 107:465-476 (2001).
Singh et al., "Absorption and translocation of glyphosate with conventional and organosilicone adjuvants," Weed Biology and Management, 8:104-111 (2008).
Snead et al., "Molecular Basis for Improved Gene Silencing by Dicer Substrate Interfering RNA Compared With Other siRNA Variants," Nucleic Acids Research, 41(12):6209-6221 (2013).
Steeves et al., "Transgenic soybeans expressing siRNAs specific to a major sperm protein gene suppress Heterodera glycines reproduction," Funct. Plant Biol., 33:991-999 (2006).
Strat et al., "Specific and nontoxic silencing in mammalian cells with expressed long dsRNAs," Nucleic Acids Research, 34(13):3803-3810 (2006).
Street, "Why is DNA (and not RNA) a Stable Storage Form for Genetic Information?," Biochemistry Revisited, pp. 1-4 (2008).
Sudarsan et al., "Metabolite-binding RNA domains are present in the genes of eukaryotes," RNA, 9:644-647 (2003).
Sun et al., "A Highly efficient Transformation Protocol for Micro-Tom, a Model Cultivar for Tomato Functional Genomics," Plant Cell Physiol., 47(3):426-431 (2006).
Supplementary European Search Report for EP 12831567.8 dated Jan. 29, 2015.
Supplementary European Search Report for EP 12832415.9 dated Jan. 21, 2015.
Sutton et al., "Activity of Mesotrione on Resistant Weeds in Maize," Pest Manag. Sci., 58:981-984 (2002).
Takasaki et al., "An Effective Method for Selecting siRNA Target Sequences in Mammalian Cells," Cell Cycle, 3:790-795 (2004).
Tank Mixing Chemicals Applied to Peanut Crops: Are the Chemicals. Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Templeton et al., "Improved DNA: liposome complexes for increased systemic delivery and gene expression," Nature Biotechnology, 15:647-652 (1997).
Tepfer, "Risk assessment of virus resistant transgenic plants," Annual Review of Phytopathology, 40:467-491 (2002).
The Seed Biology Place, Website Gerhard Leubner Lab Royal Holloway, University of London, http://www.seedbiology.de/seedtechnology.asp, last updated May 2, 2012.
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Timmons et al., "Specific interference by ingested dsRNA," Nature, 395:854 (1998).
Topfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts", Biotechnology, 1988, pp. 1072-1074, vol. 6.
Tran et al., "Control of specific gene expression in mammalian cells by co-expression of long complementary RNAs," FEBS Lett. ;573(1-3):127-134 (2004).
Tranel et al., "Resistance of Weeds to ALS-Inhibiting Herbicides: What Have We Learned?," Weed Science, 50:700-712 (2002).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Urayama et al., "Knock-down of OsDCL2 in Rice Negatively Affects Maintenance of the Endogenous dsRNA Virus, *Oryza sativa* Endomavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The Contributions of dsRNA Structure to Dicer Specificity and Efficiency," RNA, 11 (5):674-682 (2005).
Vert et al., "An accurate and interpretable model for siRNA efficacy prediction," BMC Bioinformatics, 7:520 (2006).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65 (1):1-9 (1999).
Wan et al., "Generation of Large Numbers of Independently Transformed Fertile Barley Plants," Plant Physiol., 104:37-48 (1994).
Waterhouse et al., "Virus resistance and gene silencing in plants can be induced by simultaneous expression of sense and antisense RNA," Proc Natl Acad Sci USA, 95:13959-13964 (1998).
Welch et al., "Expression of ribozymes in gene transfer systems to modulate target RNA levels," Curr Opin Biotechnol. 9(5):486-496 (1998).
Written Opinion dated May 8, 2014, in International Application No. PCT/IL2013/050447.
Written Opinion dated Sep. 4, 2014, in Singapore Patent Application No. 201206152-9.
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "A novel rice gene, NRR responds to macronutrient deficiency and regulates root growth," Mol Plant, 5(1):63-72 (2012).
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Wang et al., "A Web-Based Design Center for Vector-Based siRNA and siRNA Cassette", BioInformatic Applications Note, 2004, pp. 1818-1820, vol. 20 No. 11.
Kozomara et al., "miRBase: Annotating High Confidence MicroRNAs Using Deep Sequencing Data", Nucleic Acids Research, 2014, p. D68-D73, vol. 42.
Mallory et al., "MicroRNA Control of PHABULOSA in Leaf Development: Importance of Pairing to the MicroRNA 5' Region", The EMBO Journal, 2004, pp. 3356-3364, vol. 23 No. 16.

(56) References Cited

OTHER PUBLICATIONS

Lu et al., "Novel and Mechanical Stress-Responsive MicroRNAs in Populus Trichocarpa That are Absent from *Arabidopsis*", The Plant Cell, Aug. 2005, pp. 2186-2203, vol. 17.
Mansoor et al., "Engineering Novel Traits in Plants Through RNA Interference", Trends in Plant Science, 2006, pp. 559-565, vol. 11, No. 11.
Dalakouras et al., "Induction of Silencing in Plants by High-Pressure Spraying of In vitro-Synthesized Small RNAs", Frontiers in Plant Science, Aug. 2016, pp. 1-5, vol. 7, No. 1327.
Australian Government, Grains Research & Development Corporation, "Adjuvants: Oils, surfactants and other additives for farm chemicals", 2012, 52 pages.
AccuStandard, Inc., "Pesticide Standards Reference Guide", 2010, 116 pages.
Momentive Performance Materials Inc. Marketing Bulleting for Silwet L-77* Ag spray adjuvant DA Performance Additives, 2011, pp. 1-4.
Office Action for U.S. Appl. No. 13/612,985 dated Nov. 10, 2015.
Yan et al., "Sprout Vacuum-Infiltration: A Simple and Efficient Agroinoculation Method for Viru-Induced Gene Silencing in Diverse Solanaceous Species", Plant Cell Reports, Sep. 2012, pp. 1713-1722, vol. 31 Issue 9.

* cited by examiner

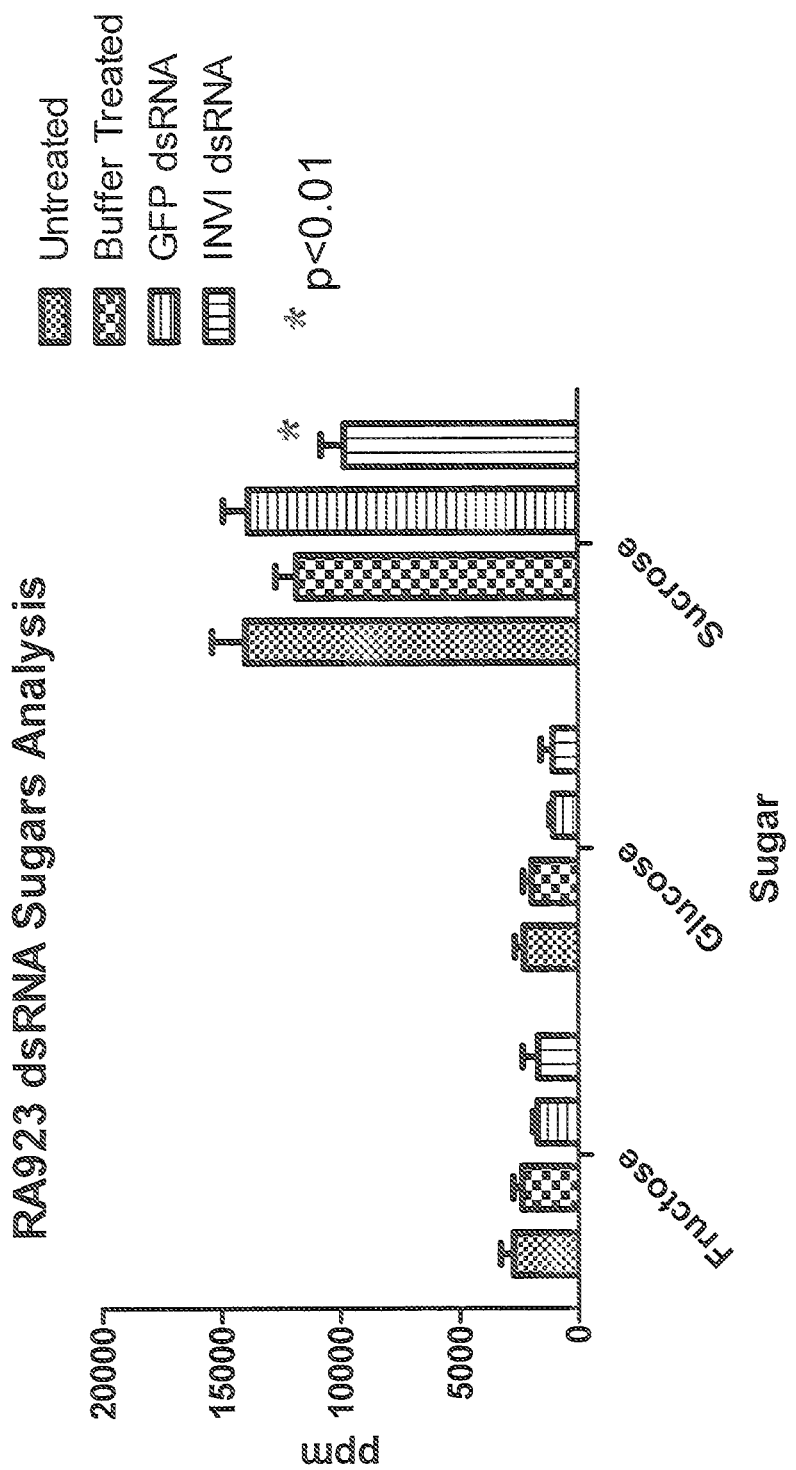

METHODS AND COMPOSITIONS FOR INCREASING INVERTASE ACTIVITY IN PLANTS

CROSS-REFERENCE TO RELATED APPLICATIONS

This non-provisional U.S. patent application claims the benefit under 35 U.S.C. § 119(e) of U.S. Provisional Patent Application No. 61/534,863, filed on Sep. 14, 2011 and incorporated herein by reference in its entirety.

INCORPORATION OF SEQUENCE LISTING

The sequence listing that is contained in the file named "40_77_58654B_ST25.txt", which is 31,265 bytes (measured in operating system MS-Windows), created on Sep. 12, 2012, is filed herewith by electronic submission and incorporated herein by reference in its entirety.

INCORPORATION BY REFERENCE OF TABLES OF PROVISIONAL APPLICATION

A "Table 2" was provided as an Appendix to U.S. Provisional Patent Application No. 61/534,863 via the USPTO's EFS system in the file named "40_77_58654_Table2.txt" which is 8,972 bytes in size (measured in MS-Windows®) that comprised SEQ ID NOs: 1-11 and is incorporated by reference herein in its entirety.

A "Table 3" was provided as an Appendix to U.S. Provisional Patent Application No. 61/534,863 via the USPTO's EFS system in the file named "40_77_58654_Table3.txt" which is 10,712 bytes in size (measured in MS-Windows®) that comprised SEQ ID NOs: 12-52 and is incorporated by reference herein in its entirety.

BACKGROUND OF THE INVENTION

Invertases mediate the hydrolysis of sucrose into glucose and fructose which are the central molecules for carbohydrate translocation, metabolism and sensing in higher plants. Plants possess three types of invertases, which are located in the apoplast, the cytoplasm and the vacuole. Extracellular and vacuolar invertase isoenzymes control many aspects of plant growth and development. For example extracellular invertase plays a crucial role in source-sink regulation and in supplying carbohydrates to sink tissues. (Tang et al., 1999; Roitsch et al., 2003) It also plays a central role in senescence. The expression of an extracellular invertase under control of the senescence-induced SAG12 promoter results in increased invertase activity in the apoplast and delays in senescence (Balibrea Lara et al., 2004 Plant cell).

Senescence is the natural process of leaf death and resource re-mobilization. It is characterized by a breakdown of cell wall components and membrane disruption leading to cellular de-compartmentalization and the loss of tissue structure. During leaf senescence, nutrients stored in the leaf are remobilized to other parts of the plant. Senescence is also an important response to biotic and a-biotic stresses and enables the recycling of valuable resources during periods of stress. Delaying senescence can have significant impacts on crop yield and quality by extending the photosynthetic period. For example increased levels of cytokinin synthesis, mediated by over-expression of the *Agrobacterium* IPT gene increased biomass by 40% and increased seed yield by 52%. (Gan and Amasino 1995 Science 270:1986-1988). In Rice, the same IPT gene was expressed under the control of a senescence associated promoter and changes in the cytokinin level led to early flowering and a greater number of emerged panicles.

Sweetness is an important consumer trait that determines the quality, flavor and marketability of fruits and vegetables. The composition and quantity of sugars primarily dictates the degree of sweetness in most fruits and vegetables. The sugar content depends upon the total solids, the PH, the fruit size and the acidity. Fructose and glucose are the major sugars in most fruits. One way to increase the sugar content in fruits is to increase the activity of invertase. In tomato the sugar content is not only important for flavor, but it also is the major contributor to the total soluble solids content, which is a key trait for processing tomatoes. Sugar accumulation is also an important characteristic for grape species and is of major commercial importance for winemakers, grape growers and dried fruit producers. The sugar concentration in wine-making grapes is critical because it's fermentation by yeast produces the alcohol and it contributes to the flavor profile. Increasing the sugar content in grape varieties by increasing invertase activity could significantly enhance the quality of wine grape varieties (Kambiranda, D., H., et al. (2011)). Corn, Rice, peppers, lettuce, sugarcane, tomatoes and melons are some additional examples of crops that would benefit from increased sugars.

One strategy for increasing invertase activity is through down-regulation of negative effectors of invertase. Jin et al, Plant cell 2009, cloned an invertase inhibitor gene, INVINH1 from tomato, which has a 516 nucleotide open reading frame that encodes a 16 kD protein (171 amino acids with a 19 AA signal peptide at the N terminus). In tomato, the INVINH1 gene is expressed in the root, stem, sink and source leaves, the flower and 1, 10 and 20 days after flowering (DAF), with expression highest in the root and 20 DAF. Suppression of the INVINH1 gene in tomato using RNAi resulted in elevated levels of cell wall invertase activity, increased in fruit hexose levels and increases in seed weight. Delays in ABA-induced senescence were also observed in INVINH1 suppressed lines.

SUMMARY OF THE INVENTION

The present invention provides for compositions comprising polynucleotide molecules and methods for treating a plant to alter or regulate gene or gene transcript expression in the plant, for example, by providing RNA or DNA for inhibition of expression. Various aspects of the invention provide compositions comprising polynucleotide molecules and related methods for topically applying such compositions to plants to regulate endogenous genes and transgenes in a plant cell. The polynucleotides, compositions, and methods disclosed herein are useful in increasing invertase activity, increasing sugar content, and/or delaying senescence of a plant.

In an aspect of the invention, the polynucleotide molecules are provided in compositions that can permeate or be absorbed into living plant tissue to initiate systemic or local gene inhibition or regulation. In certain embodiments of the invention, the polynucleotide molecules ultimately provide to a plant, or allow the in planta production of, RNA that is capable of hybridizing under physiological conditions in a plant cell to RNA transcribed from a target endogenous gene or target transgene in the plant cell, thereby effecting regulation of the target gene. In other embodiments of the invention, the polynucleotide molecules disclosed herein are useful for ultimately providing to a plant, or allowing the in planta production of, RNA that is capable of hybridizing under physiological conditions to RNA transcribed from a target gene in a cell of the plant, thereby effecting regulation of the target gene. In certain embodiments, regulation of the target genes, such as by silencing or suppression of the target gene, leads to the upregulation of another gene that is itself affected or regulated by the target gene's expression. In certain embodiments, regulation of the target genes, such as by silencing or suppression of the target gene, leads to the upregulation of another gene that is itself affected or regulated by the target gene's expression.

In certain aspects or embodiments of the invention, the topical application of a composition comprising an exogenous polynucleotide and a transfer agent to a plant or plant part according to the methods described herein does not necessarily result in nor require the exogenous polynucleotide's integration into a chromosome of the plant. In certain aspects or embodiments of the invention, the topical application of a composition comprising an exogenous polynucleotide and a transfer agent to a plant or plant part according to the methods described herein does not necessarily result in nor require transcription of the exogenous polynucleotide from DNA integrated into a chromosome of the plant. In certain embodiments, topical application of a composition comprising an exogenous polynucleotide and a transfer agent to a plant according to the methods described herein also does not necessarily require that the exogenous polynucleotide be physically bound to a particle, such as in biolistic mediated introduction of polynucleotides associated with gold or tungsten particles into internal portions of a plant, plant part, or plant cell. An exogenous polynucleotide used in certain methods and compositions provided herein can optionally be associated with an operably linked promoter sequence in certain embodiments of the methods provided herein. However, in other embodiments, an exogenous polynucleotide used in certain methods and compositions provided herein is not associated with an operably linked promoter sequence. Also, in certain embodiments, an exogenous polynucleotide used in certain methods and compositions provided herein is not operably linked to a viral vector.

In certain embodiments, methods for increasing invertase activity, increasing sugar content and/or delaying senescence in a plant comprising topically applying compositions comprising a polynucleotide and a transfer agent that suppress the target INVINH1 gene are provided. In certain embodiments, methods for selectively suppressing the target INVINH1 gene by topically applying the polynucleotide composition to a plant surface at one or more selected seed, vegetative, or reproductive stage(s) of plant growth are provided. Such methods can provide for gene suppression in a plant or plant part on an as needed or as desired basis. In certain embodiments, methods for selectively suppressing the target INVINH1 gene by topically applying the polynucleotide composition to a plant surface at one or more pre-determined seed, vegetative, or reproductive stage(s) of plant growth are provided. Such methods can provide for gene suppression in a plant or plant part that obviates any undesired or unnecessary effects of suppressing the genes expression at certain seed, vegetative, or reproductive stage(s) of plant development.

In certain embodiments, methods for selectively increasing invertase activity, increasing sugar content and/or delaying senescence in a plant by topically applying the polynucleotide composition to the plant surface at one or more selected seed, vegetative, or reproductive stage(s) are provided. Such methods can provide for the increased invertase activity, increased sugar content and/or delayed senescence in a plant or plant part on an as needed or as desired basis. In certain embodiments, methods for selectively increasing invertase activity, increasing sugar content and/or delaying senescence in a plant by topically applying the polynucleotide composition to the plant surface at one or more predetermined seed, vegetative, or reproductive stage(s) are provided. Such methods can provide for the increased invertase activity, increased sugar content and/or delayed senescence in a plant or plant part that obviates any undesired or unnecessary effects of providing the increased invertase activity, increased sugar content and/or delayed senescence at certain seed, vegetative, or reproductive stage(s) of plant development.

Polynucleotides that can be used to suppress an INVINH1 gene include, but are not limited to, any of: i) polynucleotides comprising at least 18 contiguous nucleotides that are essentially identical or essentially complementary to an INVINH1 gene or to a transcript of the genes of Tables 1 or 2 (SEQ ID NO: 1-11); ii) polynucleotides comprising at least 18 contiguous nucleotides that are essentially identical or essentially complementary to SEQ ID NO: 65 or a polynucleotide of Table 3 (SEQ ID NO: 12-52); or, iii) polynucleotides comprising at least 18 contiguous nucleotides that are essentially identical or essentially complementary to a polynucleotide of Table 4 (SEQ ID NO: 53-64).

Certain embodiments of the invention are drawn to methods for producing a plant exhibiting increased invertase activity, increased sugar content and/or delayed senescence. Such methods comprise the steps of topically applying to a plant surface a composition that comprises: (a) at least one polynucleotide that comprises at least 18 contiguous nucleotides that are essentially identical or essentially complementary to an INVINH1 gene or to a transcript of said gene; and (b) a transfer agent, wherein said plant exhibits increased invertase activity, increased sugar content and/or delayed senescence that results from suppression of said INVINH1 gene. In certain embodiments of such methods, the polynucleotide molecule comprises sense ssDNA, sense ssRNA, dsRNA, dsDNA, a double stranded DNA/RNA hybrid, anti-sense ssDNA, or anti-sense ssRNA. In certain embodiments of such methods, the polynucleotide is selected from the group consisting of SEQ ID NO: 12-64, and 65, or the polynucleotide comprises at least 18 contiguous nucleotides that are essentially identical or essentially complementary to SEQ ID NO: 1-11, or the polynucleotide comprises at least 18 contiguous nucleotides that are essentially identical or essentially complementary to SEQ ID NO: 12-65. In certain embodiments of such methods, a plant used is a *Capsicum*, glycine, *Nicotiana, Solanum*, or *vitis* plant, said gene or said transcript is a INVINH1 gene or transcript such as from a corresponding plant, and said polynucleotide molecule is selected from SEQ ID NO; 65 of from Table 3 (SEQ ID NO: 12-52). In certain embodiments of such methods, a plant used is a *Capsicum*, glycine, *Nicotiana, Solanum*, or *vitis* plant, said gene or said transcript is a INVINH1 gene or transcript such as from a corresponding plant, and said polynucleotide molecule comprises at least 18 contiguous nucleotides that are essentially identical or essentially complementary to a corresponding gene of Table 2 (SEQ ID NO: 1-11). In certain embodiments of such methods, a plant used is a plant of Table 4, said gene or said transcript is a INVINH1 gene or transcript such as from a corresponding plant, and said polynucleotide molecule comprises at least 18 contiguous nucleotides that are essentially identical or essentially complementary to a polynucleotide of Table 4 (SEQ ID NO: 53-64). In certain embodiments, the composition comprises any combination of two or more polynucleotide molecules. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the composition further comprises a non-polynucleotide herbicidal molecule when a plant is resistant to said herbicidal molecule. In certain embodiments, the transfer agent comprises an organosilicone preparation. In certain embodiments, the polynucleotide is not operably linked to a viral vector. In certain embodiments, the polynucleotide is not integrated into the plant chromosome.

Certain embodiments of the invention are drawn to one or more plants obtained by a method of the invention such as the methods of the preceding embodiments. In certain embodiments, a plant obtained by such methods exhibits increased invertase activity, increased sugar content and/or delayed senescence. In certain embodiments, a progeny plant or a plant part derived therefrom—of a plant obtained by a method the invention—exhibits increased invertase activity, increased sugar content and/or delayed senescence. Certain embodiments are drawn to a progeny plant of a plant obtained by a method the invention, wherein the progeny plant exhibits increased invertase activity, increased sugar content and/or delayed senescence. Certain embodiments are drawn to a seed of a plant obtained by a method of the invention, wherein the seed exhibits increased invertase activity, increased sugar content and/or delayed senescence. Certain embodiments are drawn to a processed product of a plant obtained by a method of the invention, wherein the processed product exhibits increased invertase activity, increased sugar content and/or delayed senescence. Certain embodiments are drawn to a processed product of a progeny plant as described herein, such as described above, wherein the processed product exhibits increased invertase activity, increased sugar content and/or delayed senescence. Certain embodiments are drawn to a processed product of a seed, such as a seed as described above, wherein the processed product exhibits increased invertase activity, increased sugar content and/or delayed senescence.

Certain embodiments are drawn to a composition comprising a polynucleotide molecule that comprises at least 18 contiguous nucleotides that are essentially identical or essentially complementary to an INVINH1 gene or transcript of said gene, wherein said polynucleotide is not operably linked to a promoter; and, a transfer agent. In certain embodiments, the polynucleotide is selected from the group consisting of SEQ ID NO: 12-64, and 65, or the polynucleotide comprises at least 18 contiguous nucleotides that are essentially identical or essentially complementary to SEQ ID NO: 1-11, or the polynucleotide comprises at least 18 contiguous nucleotides that are essentially identical or essentially complementary to SEQ ID NO: 12-65. In certain embodiments, (a) a plant is a *capsicum*, glycine, *Nicotiana, Solanum*, or *vitis* plant, a gene or transcript is a INVINH1 gene or transcript, such as from a corresponding plant, and the polynucleotide molecule is selected from SEQ ID NO: 65 or from Table 3 (SEQ ID NO: 12-52), or said polynucleotide molecule comprises at least 18 contiguous nucleotides that are essentially identical or essentially complementary to a corresponding gene of Table 2 (1-11), or said polynucleotide molecule comprises at least 18 contiguous nucleotides that are essentially identical or essentially complementary to SEQ ID NO: 12-65; or (b) said plant is a plant of Table 4 and said polynucleotide molecule comprises at least 18 contiguous nucleotides that are essentially identical or essentially complementary to a polynucleotide of Table 4 (53-64). In certain embodiments of the composition the polynucleotide is at least 18 to about 24, about 25 to about 50, about 51 to about 100, about 101 to about 300, about 301 to about 500, or at least about 500 or more residues in length. In certain embodiments of the composition, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the transfer agent is an organosilicone preparation. In certain embodiments of the composition, the polynucleotide is not physically bound to a biolistic particle.

Certain embodiments of the invention are drawn to methods of making a composition comprising the step of combining at least: a) a polynucleotide molecule comprising at least 18 contiguous nucleotides that are essentially identical or essentially complementary to an INVINH1 gene or a transcript of said gene, wherein said polynucleotide is not operably linked to a promoter or a viral vector; and, b) a transfer agent. In certain embodiments, the polynucleotide is obtained by in vivo biosynthesis, in vitro enzymatic synthesis, or chemical synthesis. In certain embodiments, the method further comprises combining with said polynucleotide and said transfer agent at least one of a non-polynucleotide herbicidal molecule, a polynucleotide herbicidal molecule, an insecticide, a fungicide, and/or a nematocide. In certain embodiments, the transfer agent is an organosilicone preparation.

Certain embodiments of the invention are drawn to methods of identifying a polynucleotide for increasing invertase activity, increasing sugar content and/or delaying senescence in a plant comprising; a) selecting a population of polynucleotides that are essentially identical or essentially complementary to an INVINH1 gene or transcript of said gene; b) topically applying to a surface of at least one of said plants a composition comprising at least one polynucleotide from said population and a transfer agent to obtain a treated plant; and, c) identifying a treated plant that exhibits suppression of the INVINH1 gene or exhibits increased invertase activity, increased sugar content and/or delayed senescence, thereby identifying a polynucleotide that increases invertase activity, increases sugar content and/or delays senescence in a plant. In certain embodiments, the polynucleotide is selected from the group consisting of SEQ ID NOs: 12-64, and 65, or the polynucleotide comprises at least 18 contiguous nucleotides that are essentially identical or essentially complementary to SEQ ID NOs: 1-11, or the polynucleotide comprises at least 18 contiguous nucleotides that are essentially identical or essentially complementary to SEQ ID NO: 12-65. In certain embodiments: (a) a plant is a *capsicum*, glycine, *Nicotiana, Solanum*, or *vitis* plant, a gene or transcript is a INVINH1 gene or transcript from the corresponding plant, and the polynucleotide molecule is selected from SEQ ID NO: 65 or Table 3 (SEQ ID NO: 12-52), or the polynucleotide molecule comprises at least 18 contiguous nucleotides that are essentially identical or essentially complementary to a corresponding gene of Table 2 (SEQ ID NO: 1-11), or the polynucleotide comprises at least 18 contiguous nucleotides that are essentially identical or essentially complementary to SEQ ID NO: 12-65; or (b) said plant is a plant of Table 4 and said polynucleotide molecule comprises at least 18 contiguous nucleotides that are essentially identical or essentially complementary to a polynucleotide of Table 4 (SEQ ID NO: 53-64).

Certain embodiments of the invention are drawn to one or more plants comprising an exogenous polynucleotide that comprises at least 18 contiguous nucleotides that are essentially identical or essentially complementary to an INVINH1 gene or a transcript of said gene, wherein said exogenous polynucleotide is not operably linked to a promoter or to a viral vector, is not integrated into the chromosomal DNA of the plant, and is not found in a non-transgenic plant; and, wherein said plant exhibits increased invertase activity, increased sugar content and/or delayed senescence that results from suppression of the INVINH1 gene. In certain embodiments, the plant further comprises an organosilicone compound or a component thereof. In certain embodiments, the polynucleotide is selected from the group consisting of SEQ ID NOs: 12-64, and 65, or the polynucleotide comprises at least 18 contiguous nucleotides that are essentially identical or essentially complementary to SEQ ID NOs: 1-11, or the polynucleotide comprises at least 18 contiguous nucleotides that are essentially identical or essentially complementary to SEQ ID NOs: 12-65. In certain embodiments, (a) a plant is a *capsicum*, glycine, *Nicotiana, Solanum*, or *vitis* plant, a gene or transcript is a INVINH1 gene gene or transcript from the corresponding plant, and a polynucleotide molecule is selected from SEQ ID NO: 65 or Table 3 (SEQ ID NO: 12-52), or the polynucleotide molecule comprises at least 18 contiguous nucleotides that are essentially identical or essentially complementary to a corresponding gene of Table 2 (SEQ ID NO: 1-11), or the polynucleotide comprises at least 18 contiguous nucleotides that are essentially identical or essentially complementary to SEQ ID NOs: 12-65; or (b) said plant is a plant of Table 4 and said polynucleotide molecule comprises at least 18 contiguous nucleotides that are essentially identical or essentially complementary to a polynucleotide of Table 4 (SEQ ID NO: 53-64).

Certain embodiments of the invention are drawn to a plant part comprising an exogenous polynucleotide that comprises at least 18 contiguous nucleotides that are essentially identical or essentially complementary to an INVINH1 gene or a transcript of said gene, wherein said exogenous polynucleotide is not operably linked to a promoter or to a viral vector and is not found in a non-transgenic plant; and, wherein said plant part exhibits increased invertase activity, increased sugar content and/or delayed senescence that results from suppression of the INVINH1 gene. In certain embodiments, the plant part further comprises an organosilicone compound or a metabolite thereof. In certain embodiments, the polynucleotide is selected from the group consisting of SEQ ID NOs: 12-64, and 65, or the polynucleotide comprises at least 18 contiguous nucleotides that are essentially identical or essentially complementary to SEQ ID NOs: 1-11, or the polynucleotide comprises at least 18 contiguous nucleotides that are essentially identical or essentially complementary to SEQ ID NOs: 12-65. In certain embodiments of a plant part, (a) a plant is a *Capsicum*, glycine, *Nicotiana, Solanum*, or *vitis* plant, a gene or transcript is a INVINH1 gene or transcript from the corresponding plant, and the polynucleotide molecule is selected from SEQ ID NO: 65 or from Table 3 (SEQ ID NO: 12-52), or the polynucleotide molecule comprises at least 18 contiguous nucleotides that are essentially identical or essentially complementary to a corresponding gene of Table 2 (SEQ ID NO: 1-11), or the polynucleotide comprises at least 18 contiguous nucleotides that are essentially identical or essentially complementary to SEQ ID NOs: 12-65; or (b) a plant is a plant of Table 4 and said polynucleotide molecule comprises at least 18 contiguous nucleotides that are essentially identical or essentially complementary to a polynucleotide of Table 4 (SEQ ID NO: 52-64). In certain embodiments, the plant part is a flower, stem, tuber, fruit, anther, pollen, leaf, root, meristem, ovule, or seed. In certain embodiments, the plant part is a seed. Certain embodiments are drawn to a processed plant product obtained from any of the plant parts of the invention. In certain embodiments, a product is a meal, a pulp, a feed, or a food product.

Certain embodiments of the invention are drawn to plants that exhibit increased invertase activity, increased sugar content and/or delayed senescence, wherein said plant was topically treated with a composition that comprises: (a) at least one polynucleotide that comprises at least 18 contiguous nucleotides that are essentially identical or essentially complementary to an INVINH1 gene or to a transcript of said gene; and, (b) a transfer agent; and, wherein said plant exhibits increased invertase activity, increased sugar content and/or delayed senescence that results from suppression of said INVINH1 gene. In certain embodiments, the transfer agent comprises an organosilicone preparation.

BRIEF DESCRIPTION OF THE DRAWINGS

FIG. 1 is a graph of sugar analysis.

BRIEF DESCRIPTION OF THE SEQUENCES

SEQ ID NOs: 1-11 are target gene sequences of various embodiments of the invention. Table 2, listing SEQ ID NOs: 1-11, was provided as an Appendix to U.S. Provisional Patent Application No. 61/534,863 via the USPTO's EFS system in the file named "40_77_58654_Table2.txt" which is 8,972 bytes in size (measured in MS-Windows®) that comprised SEQ ID NOs: 1-11 and is incorporated by reference herein in its entirety.

SEQ ID NO: 12-52 are trigger sequences of various embodiments of the invention. Table 3, listing SEQ ID NO: 12-52, was provided as an Appendix to U.S. Provisional Patent Application No. 61/534,863 via the USPTO's EFS system in the file named "40_77_58654_Table3.txt" which is 10,712 bytes in size (measured in MS-Windows®) that comprised SEQ ID NOs: 12-52 and is incorporated by reference herein in its entirety.

SEQ ID NOs: 53-64 are 21-mer polynucleotide trigger sequences of the target gene INVINH1 common to various plant species (see Table 4 herein).

SEQ ID NO: 65 is a 250 bp fragment of tomato Invertase Inhibitor (from SEQ ID NO: 9).

SEQ ID NO: 66 is an oligonucleotide primer containing T7 promoter sequence and complementary to 5' strand of SEQ ID NO: 65.

SEQ ID NO: 67 is an oligonucleotide primer containing T7 promoter sequence and complementary to 3' strand of SEQ ID NO: 65.

SEQ ID NO: 68 is a 184 bp fragment of GFPDNA.

DETAILED DESCRIPTION

I. Definitions

The following definitions and methods are provided to better define the present invention and to guide those of ordinary skill in the art in the practice of the present invention. Unless otherwise noted, terms are to be understood according to conventional usage by those of ordinary skill in the relevant art.

Where a term is provided in the singular, the inventors also contemplate aspects of the invention described by the plural of that term.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "DNA nucleotide sequence," and "DNA polynucleotide sequence" refer to the nucleotide sequence of a DNA molecule.

As used herein, the term "gene" refers to any portion of a nucleic acid that provides for expression of a transcript or encodes a transcript. A "gene" thus includes, but is not limited to, a promoter region, 5' untranslated regions, transcript encoding regions that can include intronic regions, and 3' untranslated regions.

As used herein, the terms "RNA," "RNA molecule," and "RNA polynucleotide molecule" refer to a single-stranded RNA or double-stranded RNA molecule of genomic or synthetic origin, such as, a polymer of ribonucleotide bases that comprise single or double stranded regions.

Unless otherwise stated, nucleotide sequences in the text of this specification are given, when read from left to right, in the 5' to 3' direction. The nomenclature used herein is that required by Title 37 of the United States Code of Federal Regulations §1.822 and set forth in the tables in WIPO Standard ST.25 (1998), Appendix 2, Tables 1 and 3.

As used herein, a "plant surface" refers to any exterior portion of a plant. Plant surfaces thus include, but are not limited to, the surfaces of flowers, stems, tubers, fruit, anthers, pollen, leaves, roots, or seeds. A plant surface can be on a portion of a plant that is attached to other portions of a plant or on a portion of a plant that is detached from the plant.

As used herein, the phrase "polynucleotide is not operably linked to a promoter" refers to a polynucleotide that is not covalently linked to a polynucleotide promoter sequence that is specifically recognized by either a DNA dependent RNA polymerase II protein or by a viral RNA dependent RNA polymerase in such a manner that the polynucleotide will be transcribed by the DNA dependent RNA polymerase II protein or viral RNA dependent RNA polymerase. A polynucleotide that is not operably linked to a promoter can be transcribed by a plant RNA dependent RNA polymerase.

As used herein, SEQ ID NOs: 12-52, though displayed in the incorporated Sequence Listing in the form of ssDNA, encompass dsDNA equivalents, dsRNA equivalents, ssRNA equivalents, ssRNA complements, ssDNA as shown, and ssDNA complements.

As used herein, SEQ ID NOs: 53-64, though displayed in the incorporated Sequence Listing in the form of ssDNA, encompass dsDNA equivalents, dsRNA equivalents, ssRNA equivalents, a ssRNA complement, ssDNA as shown, and ssDNA complements.

As used herein, SEQ ID NOs: 65 and 68, though displayed in the incorporated Sequence Listing in the form of ssDNA, encompass dsDNA equivalents, dsRNA equivalents, ssRNA equivalents, a ssRNA complement, ssDNA as shown, and ssDNA complements.

As used herein, a first nucleic-acid sequence is "operably" connected or "linked" with a second nucleic acid sequence when the first nucleic acid sequence is placed in a functional relationship with the second nucleic acid sequence. For instance, a promoter is operably linked to an RNA and/or protein-coding sequence if the promoter provides for transcription or expression of the RNA or coding sequence. Generally, operably linked DNA sequences are contiguous and, where necessary to join two protein-coding regions, are in the same reading frame.

As used herein, the phrase "organosilicone preparation" refers to a liquid comprising one or more organosilicone compounds, wherein the liquid or components contained therein, when combined with a polynucleotide in a composition that is topically applied to a target plant surface, enable the polynucleotide to enter a plant cell. Exemplary organosilicone preparations include, but are not limited to, preparations marketed under the trade names "Silwet®" or "BREAK-THRU®" and preparations provided in Table 5. In certain embodiments, an organosilicone preparation can enable a polynucleotide to enter a plant cell in a manner permitting a polynucleotide mediated suppression of target gene expression in the plant cell.

As used herein, the phrase "provides for increased invertase activity" "increasing invertase activity," and the like refers to any measurable increase in a plant's invertase activity or the measurable invertase activity in a part of the plant such as its fruit or seed or in a processed product derived from the plant or part of the plant. In certain embodiments, an increase in invertase activity in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants. It is also understood that such comparison could also be done with products derived from plants or plant parts.

As used herein, the phrase "provides for increased sugar content" "increasing sugar content," and the like refers to any measurable increase in at least glucose and fructose content of a plant or the measurable sugar content in a part of the plant such as its fruit or seed or in a processed product derived from the plant or part of the plant. In certain embodiments, increased sugar content in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants. It is also understood that such comparison could also be done with products derived from plants or plant parts.

As used herein, the phrase "provides for delayed senescence" "delaying senescence," and the like refers to any measurable delay in senescence of a plant or in a part of the plant such as its fruit or seed or in a processed product derived from the plant or part of the plant. In certain embodiments, delayed senescence in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants. It is also understood that such comparison could also be done with processed products derived from plants or plant parts.

As used herein, the phrase "provides for a reduction", when used in the context of a transcript or a protein in a plant or plant part, refers to any measurable decrease in the level of transcript or protein in a plant or plant part. In certain embodiments, a reduction of the level of a transcript or protein in a plant or plant part can be determined in a comparison to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the phrase "wherein said plant does not comprise a transgene" refers to a plant that lacks either a DNA molecule comprising a promoter that is operably linked to a polynucleotide or a recombinant viral vector.

As used herein, the phrase "suppressing expression" or "suppression", when used in the context of a gene, refers any measurable decrease in the amount and/or activity of a product encoded by the gene. Thus, expression of a gene can be suppressed when there is a reduction in levels of a transcript from the gene, a reduction in levels of a protein encoded by the gene, a reduction in the activity of the transcript from the gene, a reduction in the activity of a protein encoded by the gene, any one of the preceding conditions, or any combination of the preceding conditions. In this context, the activity of a transcript includes, but is not limited to, its ability to be translated into a protein and/or to exert any RNA-mediated biologic or biochemical effect. In this context, the activity of a protein includes, but is not limited to, its ability to exert any protein-mediated biologic or biochemical effect. In certain embodiments, a suppression of gene expression in a plant or plant part can be determined in a comparison of gene product levels or activities in a treated plant to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, the term "liquid" refers to both homogeneous mixtures such as solutions and non-homogeneous mixtures such as suspensions, colloids, micelles, and emulsions.

II. Overview

Provided herein are certain methods and polynucleotide compositions that can be applied to living plant cells/tissues to suppress expression of target genes and that provide increased invertase activity, increased sugar content and/or delayed senescence to a crop plant in need of the benefit. Also provided herein are plants and plant parts exhibiting increased invertase activity, increased sugar content and/or delayed senescence as well as processed products of such plants or plant parts. The compositions may be topically applied to the surface of a plant, such as to the surface of a leaf, and include a transfer agent. Aspects of the method can be applied to various crops, for example, including but not limited to: i) row crop plants including, but not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants. Fruit trees produced by such processes include, but are not limited to, citrus and apple trees. Plants produced by such processes include, but are not limited to, avocados, tomatoes, eggplant, cucumber, melons, watermelons, and grapes as well as various ornamental plants.

Without being bound by theory, the compositions and methods of the present invention are believed to operate through one or more of the several natural cellular pathways involved in RNA-mediated gene suppression as generally described in Brodersen and Voinnet (2006), *Trends Genetics*, 22:268-280; Tomari and Zamore (2005) *Genes & Dev.*, 19:517-529; Vaucheret (2006) *Genes Dev.*, 20:759-771; Meins et al. (2005) *Annu. Rev. Cell Dev. Biol.*, 21:297-318; and Jones-Rhoades et al. (2006) *Annu. Rev. Plant Biol.*, 57:19-53. RNA-mediated gene suppression generally involves a double-stranded RNA (dsRNA) intermediate that is formed intra-molecularly within a single RNA molecule or inter-molecularly between two RNA molecules. This longer dsRNA intermediate is processed by a ribonuclease of the RNAase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 to 24 base pairs (See, Hamilton et al. (2002) *EMBO J.*, 21:4671-4679).

In certain embodiments, methods provided herein can permit control of the timing or frequency of polynucleotide application(s). Timing the gene suppression to such conditions will allow optimal yield results, and will avoid unwanted effects on plant development or disease resistance.

Polynucleotides

As used herein, "polynucleotide" refers to a DNA or RNA molecule containing multiple nucleotides and generally refers both to "oligonucleotides" (a polynucleotide molecule of 18-25 nucleotides in length) and longer polynucleotides of 26 or more nucleotides. Embodiments of this invention include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments of this invention include compositions including oligonucleotides, polynucleotides, or a mixture of both, including: RNA or DNA or RNA/DNA hybrids or chemically modified oligonucleotides or polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g, fluorescein or rhodamine) or other label (e. g., biotin).

Polynucleotides can be single- or double-stranded RNA, single- or double-stranded DNA, double-stranded DNA/RNA hybrids, and modified analogues thereof. In certain embodiments of the invention, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand will comprise at least 18 nucleotides that are essentially complementary to the target gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain embodiments, the polynucleotides can be operably linked to a promoter—generally a promoter functional in a plant, for example, a pol II promoter, a pol III promoter, a pol IV promoter, or a pol V promoter.

The polynucleotide molecules of the present invention are designed to modulate expression by inducing regulation or suppression of an endogenous gene in a plant and are designed to have a nucleotide sequence essentially identical or essentially complementary to the nucleotide sequence of an endogenous gene of a plant or to the sequence of RNA transcribed from an endogenous gene of a plant, which can be coding sequence or non-coding sequence. These effective polynucleotide molecules that modulate expression are referred to herein as "a trigger, or triggers". By "essentially identical" or "essentially complementary" it is meant that the trigger polynucleotides (or at least one strand of a double-stranded polynucleotide) have sufficient identity or complementarity to the endogenous gene or to the RNA transcribed from the endogenous gene (e.g. the transcript) to suppress expression of the endogenous gene (e.g. to effect a reduction in levels or activity of the gene transcript and/or encoded protein). Polynucleotides of the methods and compositions provided herein need not have 100 percent identity to a complementarity to the endogenous gene or to the RNA transcribed from the endogenous gene (i.e. the transcript) to suppress expression of the endogenous gene (i.e. to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g. the transcript). In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g. the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

In certain embodiments, polynucleotides used in the methods and compositions provided herein can be essentially identical or essentially complementary to any of: i) conserved regions of INVINH1 genes of both monocot and dicot plants; ii) conserved regions of INVINH1 genes of monocot plants; or iii) conserved regions of INVINH1 genes of dicot plants. Such polynucleotides that are essentially identical or essentially complementary to such conserved regions can be used to increase invertase activity, increase sugar content, and/or delay senescence by suppressing expression of INVINH1 in any of: i) both dicot and monocot plants, including, but not limited to, *capsicum*, glycine, *nicotiana, solanum* (tomato), and *vitis*. Specific regions that can be targeted by essentially identical or essentially complementary polynucleotides include, but are not limited to polynucleotides selected from the group consisting of SEQ ID NOs: 53-63 and 64 that are conserved in INVINH1 genes of various plant species.

Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to an RNA transcribed from the target gene (e.g. the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to an RNA transcribed from the target gene (e.g. the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. Nucleic Acids Research, 2005, Vol. 33, No. 5 1671-1677. In certain exemplary embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e. positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of INVINH1 expression or increased invertase activity, increased sugar content and/or delayed senescence.

In certain embodiments, polynucleotide molecules are designed to have 100 percent sequence identity with or complementarity to one allele or one family member of a given target gene (coding or non-coding sequence of a gene for INVINH1 of the present invention). In other embodiments, the polynucleotide molecules are designed to have 100 percent sequence identity with or complementarity to multiple alleles or family members of a given target gene.

In certain embodiments, polynucleotide compositions and methods provided herein typically effect regulation or modulation (e. g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or transcript encoding an INVINH1 gene of the plant are provided, whereby expression of the gene in said plant or progeny thereof is systemically suppressed in comparison to a control plant that has not been treated with the composition.

In certain embodiments, polynucleotide compositions and methods provided herein typically effect regulation or modulation (e. g., suppression) of gene expression during a period during the life of the treated plant of at least 1 week or longer in local fashion. In certain embodiments, methods of locally suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or transcript encoding an INVINH1 gene of the plant are provided, whereby expression of the gene in said plant or progeny thereof is locally suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

Tiling

Polynucleotide trigger molecules can be identified by "tiling" gene targets in random length fragments, e.g. 200-300 polynucleotides in length, with partially overlapping regions, e.g. 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

Polynucleotides fragments are designed along the length of the full length coding and untranslated regions of a INVINH1 gene or family member as contiguous overlapping fragments of 200-300 polynucleotides in length or fragment lengths representing a percentage of the target gene. These fragments are applied topically (as sense or anti-sense ssDNA or ssRNA, dsRNA, or dsDNA) to determine the relative effectiveness in providing the increased invertase activity, increased sugar content and/or delayed senescence. Fragments providing the desired activity may be further subdivided into 50-60 polynucleotide fragments which are evaluated for providing increased invertase activity, increased sugar content and/or delayed senescence. The 50-60 base fragments with the desired activity may then be further subdivided into 19-30 base fragments which are evaluated for providing increased invertase activity, increased sugar content and/or delayed senescence. Once relative effectiveness is determined, the fragments are utilized singly, or in combination in one or more pools to determine effective trigger composition or mixture of trigger polynucleotides for providing increased invertase activity, increased sugar content and/or delayed senescence.

Coding and/or non-coding sequences of INVINH1 family members in crops of interest are aligned and 200-300 polynucleotide fragments from the least homologous regions amongst the aligned sequences are evaluated using topically applied polynucleotides (as sense or anti-sense ssDNA or ssRNA, dsRNA, or dsDNA) to determine their relative effectiveness in providing increased invertase activity, increased sugar content and/or delayed senescence. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of increased invertase activity, increased sugar content and/or delayed senescence. Once relative effectiveness is determined, the fragments are utilized singly, or again evaluated in combination with one or more other fragments to determine the trigger composition or mixture of trigger polynucleotides for providing increased invertase activity, increased sugar content and/or delayed senescence.

Coding and/or non-coding sequences of INVINH1 family members in crops of interest are aligned and 200-300 polynucleotide fragments from the most homologous regions amongst the aligned sequences are evaluated using topically applied polynucleotides (as sense or anti-sense ssDNA or ssRNA, dsRNA, or dsDNA) to determine their relative effectiveness in providing increased invertase activity, increased sugar content and/or delayed senescence. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for increasing invertase activity, increasing sugar content and/or delaying senescence. Once relative effectiveness is determined, the fragments may be utilized singly, or in combination with one or more other fragments to determine the trigger composition or mixture of trigger polynucleotides for providing increased invertase activity, increased sugar content and/or delayed senescence.

Also, provided herein are methods for identifying a preferred polynucleotide for increasing invertase activity, increasing sugar content and/or delaying senescence in a plant. Populations of candidate polynucleotides that are essentially identical or essentially complementary to an INVINH1 gene or transcript of the gene can be generated by a variety of approaches, including but not limited to, any of the tiling, least homology, or most homology approaches provided herein. Such populations of polynucleotides can also be generated or obtained from any of the polynucleotides or genes provided herewith in Tables 1 or 2 (SEQ ID NOs: 1-11). Such populations of polynucleotides can also be generated or obtained from any genes that are orthologous to the genes provided herewith in Table 1. Such polynucleotides can be topically applied to a surface of plants in a composition comprising at least one polynucleotide from said population and a transfer agent to obtain treated plants. Treated plants that exhibit suppression of the INVINH1 gene and/or exhibit increased invertase activity, increased sugar content and/or delayed senescence are identified, thus identifying a preferred polynucleotide that increases invertase activity, increases sugar content and/or delays senescence in a plant. Suppression of the gene can be determined by any assay for the levels and/or activity of a gene product (i.e. transcript or protein). Suitable assays for transcripts include, but are not limited to, semi-quantitative or quantitative reverse transcriptase PCR® (qRT-PCR) assays. Suitable assays for proteins include, but are not limited to, semi-quantitative or quantitaive immunoassays, biochemical activity assays, or biological activity assays. In certain embodiments, the polynucleotides can be applied alone. In other embodiments, the polynucleotides can be applied in pools of multiple polynucleotides. When a pool of polynucleotides provides for suppression of the INVINH1 gene and/or increased invertase activity, increased sugar content and/or delayed senescence are identified, the pool can be re-replicated and re-tested as necessary or desired to identify one or more preferred polynucleotide(s) that increases invertase activity, increases sugar content and/or delays senescence in a plant.

TABLE 1

Representative target sequences for regulation of INVINH1 genes to provide increased invertase activity, increased sugar content and/or delayed senescence in plants.

| SEQ ID NO | Source | Name \| Reference | Type | Length |
|---|---|---|---|---|
| 1 | Capsicum | KS25018K16; | Partial | 444 |
| 2 | Glycine | BT090960 | CDS | 549 |
| 3 | Glycine | BT091584; | CDS | 555 |
| 4 | Glycine | Gm17:2673574 . . . 2672075; | Promoter | 1500 |
| 5 | Glycine | Gm17:2676529 . . . 2675030; | Promoter | 1500 |
| 6 | Nicotiana | NICBE-24JUN11-CLUS03250 | Partial | 399 |
| 7 | Nicotiana | Y12805; | CDS | 501 |
| 8 | Nicotiana | Y12806 | CDS | 519 |
| 9 | Solanum | AJ010943; | CDS | 516 |
| 10 | Solanum | SL2.40ch12:64774047 . . . 64775546; | Promoter | 1500 |
| 11 | Vitis | XM_002279765 | CDS | 510 |

* Sequences are provided in Table 2 of the accompanying Appendix which is hereby incorporated in its entirety herein.

Methods of making polynucleotides are well known in the art. Such methods of making polynucleotides can include in vivo biosynthesis, in vitro enzymatic synthesis, or chemical synthesis. In certain embodiments, RNA molecules can be made by either in vivo or in vitro synthesis from DNA templates where a suitable promoter is operably linked to the polynucleotide and a suitable DNA—dependent RNA polymerase is provided. DNA—dependent RNA polymerases include, but are not limited to, E. coli or other bacterial RNA polymerases as well as the bacteriophage RNA polymerases such as the T7, T3, and SP6 RNA polymerases. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end that encodes a bacteriophage T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score (Reynolds et al. Nature Biotechnology 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

While there is no upper limit on the concentrations and dosages of polynucleotide molecules that can be useful in the methods and compositions provided herein, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotide molecules is about 1 nanomole (nmol) of polynucleotide molecules per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide is applied. In certain embodiments, about 0.5 nmol to about 2 nmol of a dsRNA is applied. In certain embodiments, a composition containing about 0.5 to about 2.0 mg/mL, or about 0.14 mg/mL of dsRNA or ssDNA (21-mer) is applied. In certain embodiments, about 1 nmol to about 5 nmol of a dsRNA is applied to a plant. In certain embodiments, the polynucleotide composition as topically applied to the plant contains the at least one polynucleotide at a concentration of about 0.01 to about 10 milligrams per milliliter, or about 0.05 to about 2 milligrams per milliliter, or about 0.1 to about 2 milligrams per milliliter. In certain embodiments, a composition of about 0.5 to about 1.5 mg/mL of a long dsRNA polynucleotide (i.e. about 50 to about 200 or more nucleotides) is applied. Very large plants, trees, or vines may require correspondingly larger amounts of polynucleotides. When using long dsRNA molecules that can be processed into multiple oligonucleotides, lower concentrations can be used. To illustrate embodiments of the invention, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e. g., seeds, leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the $9^{th}$ Compendium of Herbicide Adjuvants, publicly available on the worldwide web (internet) at herbicide-.adjuvants.com can be used, e. g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL-.REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0:6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided. In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1%. by weight (wt percent) is used or provided.

In certain embodiments, any of the commercially available organosilicone preparations provided in the following Table 5 can be used as transfer agents in apolynucleotide composition. In certain embodiments where an organosilicone preparation of Table 5 is used as a pre-spray treatment of plant leaves or other surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation of Table 5 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

TABLE 5

| Name | CAS number | Manufacturer [1,2] |
|---|---|---|
| BREAK-THRU ® S 321 | na | Evonik Industries AG |
| BREAK-THRU ® S 200 | 67674-67-3 | Evonik Industries AG |
| BREAK-THRU ® OE 441 | 68937-55-3 | Evonik Industries AG |
| BREAK-THRU ® S 278 | 27306-78-1 | Evonik Goldschmidt |
| BREAK-THRU ® S 243 | na | Evonik Industries AG |
| Silwet ® L-77 | 27306-78-1 | Momentive Performance Materials |
| Silwet ® HS 429 | na | Momentive Performance Materials |
| Silwet ® HS 312 | na | Momentive Performance Materials |
| BREAK-THRU ® S 233 | 134180-76-0 | Evonik Industries AG |
| Silwet ® HS 508 | | Momentive Performance Materials |
| Silwet ® HS 604 | | Momentive Performance Materials |

[1] Evonik Industries AG, Essen, Germany

[2] Momentive Performance Materials, Albany, New York

Organosilicone preparations used in the methods and compositions provided herein can comprise one or more effective organosilicone compounds. As used herein, the phrase “effective organosilicone compound” is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length “n” of about “7.5”. In certain embodiments, the average chain length “n” can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

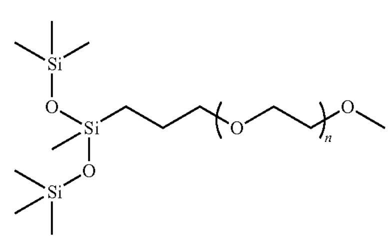

(Compound I: polyalkyleneoxide heptamethyltrisiloxane, average n=7.5).

One organosilicone compound believed to be ineffective comprises the formula:

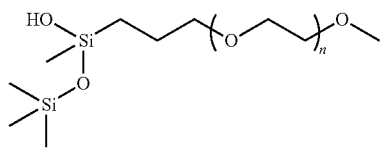

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, the polynucleotide compositions that comprise an organosilicone preparation can comprise a salt such as ammonium chloride, tetrabutylphosphonium bromide, and/or ammonium sulfate. Ammonium chloride, tetrabutylphosphonium bromide, and/or ammonium sulfate can be provided in the polynucleotide composition at a concentration of about 0.5% to about 5% (w/v). An ammonium chloride, tetrabutylphosphonium bromide, and/or ammonium sulfate concentration of about 1% to about 3%, or about 2% (w/v) can also be used in the polynucleotide compositions that comprise an organosilicone preparation. In certain embodiments, the polynucleotide compositions can comprise an ammonium salt at a concentration greater or equal to 300 millimolar. In certain embodiments, the polynucleotide compositions that comprise an organosilicone preparation can comprise ammonium sulfate at concentrations from about 80 to about 1200 mM or about 150 mM to about 600 mM.

In certain embodiments, the polynucleotide compositions can also comprise a phosphate salt. Phosphate salts used in the compositions include, but are not limited to, calcium, magnesium, potassium, or sodium phosphate salts. In certain embodiments, the polynucleotide compositions can comprise a phosphate salt at a concentration of at least about 5 millimolar, at least about 10 millimolar, or at least about 20 millimolar. In certain embodiments, the polynucleotide compositions will comprise a phosphate salt in a range of about 1 mM to about 25 mM or in a range of about 5 mM to about 25 mM. In certain embodiments, the polynucleotide compositions can comprise sodium phosphate at a concentration of at least about 5 millimolar, at least about 10 millimolar, or at least about 20 millimolar. In certain embodiments, the polynucleotide compositions can comprise sodium phosphate at a concentration of about 5 millimolar, about 10 millimolar, or about 20 millimolar. In certain embodiments, the polynucleotide compositions will comprise a sodium phosphate salt in a range of about 1 mM to about 25 mM or in a range of about 5 mM to about 25 mM. In certain embodiments, the polynucleotide compositions will comprise a sodium phosphate salt in a range of about 10 mM to about 160 mM or in a range of about 20 mM to about 40 mM. In certain embodiments, the polynucleotide compositions can comprise a sodium phosphate buffer at a pH of about 6.8.

In certain embodiments, other useful transfer agents or adjuvants to transfer agents that can be used in polynucleotide compositions provided herein include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the polynucleotide compositions that comprise a transfer agent are formulated with counter-ions or other molecules that are known to associate with nucleic acid molecules. Illustrative examples include, tetraalkyl ammonium ions, trialkyl ammonium ions, sulfonium ions, lithium ions, and polyamines such as spermine, spermidine, or putrescine. In certain embodiments, the polynucleotide compositions are formulated with a non-polynucleotide herbicide. Non-polynucleotide herbicidal molecules include, but are not limited to, glyphosate, auxin-like benzoic acid herbicides including dicamba, chloramben and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrionogen oxidase inhibitors, and 4-hydroxyphenyl-pyruvate-dioxygenase inhibiting herbicides.

In certain embodiments, the polynucleotides used in the compositions that are essentially identical or essentially complementary to the target gene or transcript will comprise the predominant nucleic acid in the composition. Thus in certain embodiments, the polynucleotides that are essentially identical or essentially complementary to the target gene or transcript will comprise at least about 50%, 75%, 95%, 98%, or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

Polynucleotides comprising ssDNA, dsDNA, ssRNA, dsRNA, or RNA/DNA hybrids that are essentially identical or complementary to certain plant target genes or transcripts and that can be used in compositions containing transfer agents that include, but are not limited to, organosilicone preparations, to suppress those target genes when topically applied to plants are disclosed in co-assigned U.S. patent application Ser. No. 13/042,856. Various polynucleotide herbicidal molecules, compositions comprising those polynucleotide herbicidal molecules and transfer agents that include, but are not limited to, organosilicone preparations, and methods whereby herbicidal effects are obtained by the topical application of such compositions to plants are also disclosed in co-assigned U.S. patent application Ser. No. 13/042,856, and those polynucleotide herbicidal molecules, compositions, and methods are incorporated herein by reference in their entireties. Genes encoding proteins that can provide tolerance to an herbicide and/or that are targets of a herbicide are collectively referred to herein as "herbicide target genes". Herbicide target genes include, but are not limited to, a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase, a cellulose synthase, a beta tubulin, and a serine hydroxymethyltransferase gene. The effects of applying certain compositions comprising polynucleotides that are essentially identical or complementary to certain herbicide target genes and transfer agents on plants containing the herbicide target genes was shown to be potentiated or enhanced by subsequent application of an herbicide that targets the same gene as the polynucleotide in co-assigned U.S. patent application Ser. No. 13/042,856. For example, compositions comprising polynucleotide targeting the EPSPS herbicide target gene were potentiated by glyphosate in experiments disclosed in co-assigned U.S. patent application Ser. No. 13/042,856.

In certain embodiments of the compositions and methods disclosed herein, the composition comprising a polynucleotide and a transfer agent can thus further comprise a second polynucleotide comprising at least 19 contiguous nucleotides that are essentially identical or essentially complementary to a transcript to a protein that confers resistance to a herbicide. In certain embodiments, the second polynucleotide does not comprise a polynucleotide that is essentially identical or essentially complementary to a transcript encoding a protein of a target plant that confers resistance to said herbicidal molecule. Thus, in an exemplary and non-limiting embodiment, the second polynucleotide could be essentially identical or essentially complementary to a transcript encoding a protein that confers resistance to a herbicide in a weed (such as an EPSPS encoding transcript) but would not be essentially identical or essentially complementary to a transcript encoding a protein that confers resistance to that same herbicide in a crop plant.

In certain embodiments, the polynucleotide compositions that comprise a transfer agent can comprise glycerin. Glycerin can be provided in the composition at a concentration of about 0.1% to about 1% (w/v or v/v). A glycerin concentration of about 0.4% to about 0.6%, or about 0.5% (w/v or v/v) can also be used in the polynucleotide compositions that comprise a transfer agent.

In certain embodiments, the polynucleotide compositions that comprise a transfer agent can further comprise organic solvents. Such organic solvents include, but are not limited to, DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions).

In certain embodiments, the polynucleotide compositions that comprise a transfer agent can further comprise naturally derived or synthetic oils with or without surfactants or emulsifiers. Such oils include, but are not limited to, plant-sourced oils, crop oils (such as those listed in the 9th Compendium of Herbicide Adjuvants, publicly available on the world wide web at herbicide.adjuvants.com), paraffinic oils, polyol fatty acid esters, or oils with short-chain molecules modified with amides or polyamines such as polyethyleneimine or N-pyrrolidine.

In aspects of the invention, methods include one or more applications of the composition comprising a polynucleotide and a transfer agent or one or more effective components contained therein. In certain embodiments of the methods, one or more applications of a transfer agent or one or more effective components contained therein can precede one or more applications of the composition comprising a polynucleotide and a transfer agent. In embodiments where a transfer agent and/or one or more effective molecules contained therein is used either by itself as a pre-treatment or as part of a composition that includes a polynucleotide, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

Compositions and methods of the invention are useful for modulating or suppressing the expression of an endogenous target gene or transgenic target gene in a plant cell or plant. In certain embodiments of the methods and compositions provided herein, expression INVINH1 genes can be suppressed completely, partially and/or transiently to result in increased invertase activity, increased sugar content and/or delayed senescence. In various embodiments, a target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes of the present invention include, but are not limited to, endogenous plant genes listed in Table 1.

Target genes and plants containing those target genes can be obtained from: i) row crop plants including, but are not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants that include, but are not limited to, citrus, apples, avocados, tomatoes, eggplant, cucumber, melons, watermelons, and grapes as well as various ornamental plants. Such row crop, vegetable, culinary, fruit, tree, or ornamental plants exhibiting increased invertase activity, increased sugar content and/or delayed senescence that result from suppressing INVINH1 are provided herein. Such row crop, vegetable, culinary, fruit, tree, or ornamental plant parts or processed plant products exhibiting increased invertase activity, increased sugar content and/or delayed senescence that result from suppressing expression of INVINH1 are also provided herein. Such plant parts can include, but are not limited to, flowers, stems, tubers, fruit, anthers, meristems, ovules, pollen, leaves, or seeds. Such processed plant products obtained from the plant parts can include, but are not limited to, a meal, a pulp, a feed, or a food product.

An aspect of the invention provides a method for modulating expression of an INVINH1 gene or family member in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the target gene INVINH1 gene or family member in either anti-sense or sense orientation, whereby the polynucleotide molecules permeate the interior of the plant and induce modulation of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches. In certain embodiments where the polynucleotide used in the composition comprises a promoter sequence essentially identical to, or essentially complementary to at least 18 contiguous nucleotides of the promoter of the endogenous target gene, the promoter sequence of the polynucleotide is not operably linked to another sequence that is transcribed from the promoter sequence.

Compositions comprising a polynucleotide and a transfer agent provided herein can be topically applied to a plant or plant part by any convenient method, e.g., spraying or coating with a powder, or with a liquid composition comprising any of an emulsion, suspension, or solution. Such topically applied sprays or coatings can be of either all or of any a portion of the surface of the plant or plant part. Similarly, the compositions comprising a transfer agent or other pre-treatment can in certain embodiments be applied to the plant or plant part by any convenient method, e. g., spraying or wiping a solution, emulsion, or suspension. Compositions comprising a polynucleotide and a transfer agent provided herein can be topically applied to plant parts that include, but are not limited to, flowers, stems, tubers, meristems, ovules, fruit, anthers, pollen, leaves, or seeds.

Application of compositions comprising a polynucleotide and a transfer agent to seeds is specifically provided herein. Seeds can be contacted with such compositions by spraying, misting, immersion, and the like.

In certain embodiments, application of compositions comprising a polynucleotide and a transfer agent to plants, plant parts, or seeds in particular can provide for increased invertase activity, increased sugar content and/or delayed senescence in progeny plants, plant parts, or seeds derived from those treated plants, plant parts, or seeds. In certain embodiments, progeny plants, plant parts, or seeds derived from those treated plants, plant parts, or seeds will exhibit increased invertase activity, increased sugar content and/or delayed senescence that result from suppressing expression of INVINH1. In certain embodiments, the methods and compositions provided herein can provide for increased invertase activity, increased sugar content and/or delayed senescence in progeny plants or seeds as a result of epigenetically inherited suppression of INVINH1 expression. In certain embodiments, such progeny plants exhibit increased invertase activity, increased sugar content and/or delayed senescence from epigenetically inherited suppression INVINH1 expression that is not caused by a transgene where the polynucleotide is operably linked to a promoter, a viral vector, or a copy of the polynucleotide that is integrated into a non-native location in the chromosomal DNA of the plant. Without seeking to be limited by theory, progeny plants or seeds derived from those treated plants, plant parts, or seeds can exhibit increased invertase activity, increased sugar content and/or delayed senescence through an epigenetic mechanism that provides for propagation of an epigenetic condition where suppression of INVINH1 expression occurs in the progeny plants, plant parts, or plant seeds. In certain embodiments, progeny plants or seeds exhibiting increased invertase activity, increased sugar content and/or delayed senescence as a result of epigenetically inherited suppression of INVINH1 expression can also exhibit increased methylation, and in particular, increased methylation of cytosine residues, in the endogenous INVINH1 of the plant. Plant parts, including seeds, of the progeny plants that exhibit increased invertase activity, increased sugar content and/or delayed senescence as a result of epigenetically inherited suppression of INVINH1 expression, can also in certain embodiments exhibit increased methylation, and in particular, increased methylation of cytosine residues, in the endogenous INVINH1. In certain embodiments, DNA methylation levels in DNA encoding the endogenous INVINH1 can be compared in plants that exhibit increased invertase activity, increased sugar content and/or delayed senescence and control plants that do not exhibit increased invertase activity, increased sugar content and/or delayed senescence to correlate the presence of increased invertase activity, increased sugar content and/or delayed senescence to epigenetically inherited suppression of INVINH1 expression and to identify plants that comprise the epigenetically inherited increased invertase activity, increased sugar content and/or delayed senescence.

Various methods of spraying compositions on plants or plant parts can be used to topically apply to a plant surface a composition comprising a polynucleotide that comprises a transfer agent. In the field, a composition can be applied with a boom that extends over the crops and delivers the composition to the surface of the plants or with a boomless sprayer that distributes a composition across a wide area. Agricultural sprayers adapted for directional, broadcast, or banded spraying can also be used in certain embodiments. Sprayers adapted for spraying particular parts of plants including, but not limited to, leaves, the undersides of leaves, flowers, stems, male reproductive organs such as tassels, meristems, pollen, ovules, and the like can also be used. Compositions can also be delivered aerially, such as by a crop dusting airplane. In certain embodiments, the spray can be delivered with a pressurized backpack sprayer calibrated to deliver the appropriate rate of the composition. In certain embodiments, such a backpack sprayer is a carbon dioxide pressurized sprayer with a 11015 flat fan or equivalent spray nozzle with a customized single nozzle assembly (to minimize waste) at a spray pressure of about 0.25 MPa and/or any single nozzle sprayer providing an effective spray swath of 60 cm above the canopy of 3 to 12 inch tall growing plants can be used. Plants in a greenhouse or growth chamber can be treated using a track sprayer or laboratory sprayer with a 11001XR or equivalent spray nozzle to deliver the sample solution at a determined rate. An exemplary and non-limiting rate is about 140 L/ha at about 0.25 MPa pressure.

In certain embodiments, it is also contemplated that a plant part can be sprayed with the composition comprising a polynucleotide that comprises a transfer agent. Such plant parts can be sprayed either pre- or post-harvest to provide increased invertase activity, increased sugar content and/or delayed senescence in the plant part that results from suppression of INVINH1 expression. Compositions can be topically applied to plant parts attached to a plant by a spray as previously described. Compositions can be topically applied to plant parts that are detached from a plant by a spray as previously described or by an alternative method. Alternative methods for applying compositions to detached parts include, but are not limited to, passing the plant parts through a spray by a conveyor belt or trough, or immersing the plant parts in the composition.

Compositions comprising polynucleotides and transfer agents can be applied to plants or plant parts at one or more developmental stages as desired and/or as needed. Application of compositions to pre-germination seeds and/or to post-germination seedlings is provided in certain embodiments. Seeds can be treated with polynucleotide compositions provided herein by methods including, but not limited to, spraying, immersion, or any process that provides for coating, imbibition, and/or uptake of the polynucleotide composition by the seed. Seeds can be treated with polynucleotide compositions using seed batch treatment systems or continuous flow treatment systems. Seed coating systems are at least described in U.S. Pat. Nos. 6,582,516, 5,891,246, 4,079,696, and 4,023,525. Seed treatment can also be effected in laboratory or commercial scale treatment equipment such as a tumbler, a mixer, or a pan granulator. A polynucleotide composition used to treat seeds can contain one or more other desirable components including, but not limited to liquid diluents, binders to serve as a matrix for the polynucleotide, fillers for protecting the seeds during stress conditions, and plasticizers to improve flexibility, adhesion and/or spreadability of the coating. In addition, for oily polynucleotide compositions containing little or no filler, drying agents such as calcium carbonate, kaolin or bentonite clay, perlite, diatomaceous earth or any other adsorbent material can be added. Use of such components in seed treatments is described in U.S. Pat. No. 5,876,739. Additional ingredients can be incorporated into the polynucleotide compositions used in seed treatments. Such ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like that can be combined with compositions comprising a polynucleotide and a transfer agent. Further ingredients used in compositions that can be applied to seeds can be found in McCutcheon's, vol. 1, "Emulsifiers and Detergents," MC Publishing Company, Glen Rock, N.J., U.S.A., 1996 and in McCutcheon's, vol. 2, "Functional Materials," MC Publishing Company, Glen Rock, N.J., U.S.A., 1996. Methods of applying compositions to seeds and pesticidal compositions that can be used to treat seeds are described in US Patent Application publication 20080092256, which is incorporated herein by reference in its entirety.

Application of the compositions in early, mid-, and late vegetative stages of plant development is provided in certain embodiments. Application of the compositions in early, mid- and late reproductive stages is also provided in certain embodiments. Application of the compositions to plant parts at different stages of maturation is also provided.

EXAMPLES

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

Example 1. Polynucleotides of the Invention Related to the Target Gene Sequences Table 2 and the incorporated sequence listing contains representative target DNA sequences (SEQ ID NOs: 1-11) from *capsicum*, glycine, *nicotiana, solanum*, and vitisfor INVINH1. For each gene having a DNA sequence provided in Table 2 (SEQ ID NOs: 1-11), single stranded or double stranded DNA or RNA fragments in sense or antisense orientation or both are mixed with an organosilicone preparation that comprises the compositions of the topical application method. This composition is topically applied to plants to effect expression of the target genes in the specified plant to obtain improved increased invertase activity, increased sugar content and/or delayed senescence.

Example 2. Polynucleotides of the Invention Related to the Trigger Molecules A method for testing the entire sequence of each gene for selecting effective trigger molecules is described. Polynucleotides fragments are designed to cover the full length coding and untranslated regions of INVINH1 genes or family members, such as shown in Table 1, as full-length sequences or as contiguous overlapping fragments of 200-300 bases length. These fragments are applied topically as sense or anti-sense ssDNA or ssRNA. dsRNA, or dsDNA to determine the relative effectiveness in providing improved increased invertase activity, increased sugar content and/or delayed senescence. Fragments providing the desired activity are further subdivided into 50-60 polynucleotide fragments which are evaluated for providing improved increased invertase activity, increased sugar content and/or delayed senescence. The 50-60 base fragments with the desired activity are subdivided into 19-30 base fragments which are evaluated for providing improved increased invertase activity, increased sugar content and/or delayed senescence. Fragments are tested singly, or in combination in one or more pools to determine effective trigger formulations for providing improved increased invertase activity, increased sugar content and/or delayed senescence.

Trigger molecules are developed to simultaneously regulate multiple gene family members by alignment of coding and/or non-coding sequences of gene families in the crops of interest, and choosing 200-300 base fragments from the most homologous regions of the aligned sequences for evaluation in the topical application method (as sense or anti-sense ssDNA or ssRNA, dsRNA, or dsDNA) to determine their relative effectiveness in INVINH1 gene regulation and/or inducing a desired phenotype. The effective segments can be subdivided into 50-60 base fragments, prioritized by most homology, and then re-evaluated in a topical application method. The effective 50-60 base fragments can be subdivided into 19-30 base fragments, prioritized by most homology, and again evaluated for gene regulation and/or induction of increased invertase activity, increased sugar content and/or delayed senescence. Once relative effectiveness is determined, the fragments can be utilized singly, or in combination with one or more other fragments, to determine the trigger formulation for providing the desired result.

Table 3 and the incorporated sequence listing shows representative trigger molecule sequences (SEQ ID NO: 12-52) from various plant species.

Table 4 and the incorporated sequence listing shows a representative list of 21-mer polynucleotide trigger sequences of the target gene INVINH1 common to various plant species consisting of sequences SEQ ID NOs: 53-64.

TABLE 4

| SEQ ID NO | Sequence | # Species | Species |
|---|---|---|---|
| 53 | TGGAATGGTAGGTTCATCTGG | 3 | Capsicum, Nicothiana (2 varieties) |
| 54 | TGAACCTACCATTCCATCTTC | 3 | Capsicum, Nicothiana (2 varieties) |
| 55 | GATGGAATGGTAGGTTCATCT | 3 | Capsicum, Nicothiana (2 varieties) |
| 56 | GATGAACCTACCATTCCATCT | 3 | Capsicum, Nicothiana (2 varieties) |
| 57 | GAAGATGGAATGGTAGGTTCA | 3 | Capsicum, Nicothiana (2 varieties) |
| 58 | CCAGATGAACCTACCATTCCA | 3 | Capsicum, Nicothiana (2 varieties) |
| 59 | CAGATGAACCTACCATTCCAT | 3 | Capsicum, Nicothiana (2 varieties) |
| 60 | ATGGAATGGTAGGTTCATCTG | 3 | Capsicum, Nicothiana (2 varieties) |

TABLE 4-continued

| SEQ ID NO | Sequence | # Species | Species |
|---|---|---|---|
| 61 | ATGAACCTACCATTCCATCTT | 3 | Capsicum, Nicothiana (2 varieties) |
| 62 | AGATGGAATGGTAGGTTCATC | 3 | Capsicum, Nicothiana (2 varieties) |
| 63 | AGATGAACCTACCATTCCATC | 3 | Capsicum, Nicothiana (2 varieties) |
| 64 | AAGATGGAATGGTAGGTTCAT | 3 | Capsicum, Nicothiana (2 varieties) |

Example 3: Topical Application of Polynucleotide Molecules

The following examples illustrate one aspect of the invention wherein double-stranded RNA trigger molecules are topically applied to a crop plant to induce silencing of the INVINH1 gene or gene family member(s) in the plant to improve the plant's tolerance to water-limited conditions.

Tomato:

Tomato plants at the 2-leaf stage grown in a peat moss, composted bark and perlite soil mix are spotted with polynucleotides, either ssDNA and/or dsRNA oligos or long dsRNAs directed to the promoter and/or targeting the coding region of the INVINH1 gene or gene family members. A representative example of the formulation of the nucleotide solution is: 40-50 nmoles of each ssDNA oligonucleotide or 0.5-2 nmoles dsRNA; 0.3% Silwet L77; 5 mM $Na_2HPO_4$ and 2% ammonium sulfate in a final volume of 40 µL. Two mature leaves are spotted with 20 µl of the nucleotide solution for a total of 40 µL per plant.

Corn:

Corn plants are germinated in potting medium and grown in the greenhouse for approximately 10 days. Single-stranded DNA and/or dsRNA polynucleotides directed to the promoter and/or targeting the coding region of the INVINH1 gene or gene family members are spotted onto the first and second leaves. A representative example of the formulation of the nucleotide solution applied is: 40-50 nmoles of each ssDNA oligonucleotide or 0.5-2 nmoles dsRNA, 0.5% Silwet L77, 20 mM $Na_2HPO_4$ and 2% ammonium sulfate in a final volume of 50 µL. Two mature leaves are spotted with 25 µL each of the nucleotide solution for a total of 50 µL per plant.

Alternatively, corn plants grown in the greenhouse are treated at the VT stage or 20 days after pollination by spraying leaves with a solution, a representative example of is a formulation containing 0.14 mg/mL of dsRNA or ssDNA (21-mer) or 0.5 to 1.5 mg/mL long dsRNA polynucleotides targeted to the INVINH1 gene or gene family with 0.5% Silwet L77, 20 mM $Na_2HPO_4$ and 2% ammonium sulfate.

Example 4: Representative Preparation

Spray liquids may be prepared the same day as spraying. Single polynucleotides or a mixture of polynucleotides at rates of between 0.04 and 0.18 mg/ml in 20 mM potassium phosphate buffer (pH 6.8) may be added to spray liquids 15 to 50 minutes before spraying.

Example 5: Method for Measuring Invertase Enzyme Activity

Application of efficacious polynucleotides will increase invertase activity. Tomato (*Solanum lycopersicum*) plants treated with trigger molecules will be grown in pots in the greenhouse at 25 C with a 16-h photoperiod. The flowers will be tagged at anthesis to determine fruit age. To confirm that topical applications of DNA or RNA apoplastic invertase activity will be measured using sugars LC-MS/MS Analysis. Sucrose, fructose and D(+)-glucose will be purchased from Sigma Aldrich and labeled sugars including D-Glucose-$^{13}C_6$,C-$d_7$, D-Fructose-6,6-$d_2$, and D-Sucrose-$^{13}C_{12}$ will be purchased from Isotech. Ethanol (Anhydrous Solvent) and ammonium hydroxide will be obtained from J.T. Baker. Water (LC/MS grade) and acetonitrile (LC/MS grade) will be purchased from Burdick & Jackson.

Extraction

Plant tissues will be collected and frozen immediately under the liquid nitrogen. Frozen tissues will be lyophilized and ground using the Mega-Grinder into fine homogenous powders. Ground lyophilized tissues will be stored at −80° C. freezer until needed for analysis. Each sample will be weighed approximately 50±5 mg into a 2 ml 96 well format glass vial and capped with strips of 12 plug caps. The 96 well plate containing sample vials will be placed on the vortex and agitated for 15 minutes. Sugars will be extracted overnight (16 to 24 hrs) at 4° C. using 1.0 ml of extraction buffer (ethanol:water=80:20, v/v). After extraction is completed, 0.65 ml of water will be added to each vial and vortexed for 15 min followed by centrifuging for 15 min at 3000 rpm at 20° C. Approximately 600 to 750 ul of supernatant will be transferred to a 96 well filter plate (Unifilter plate, Whatman) and filtered by centrifuging. Twenty microliter of each sample will be transferred to a LC/MS certified vial followed by the addition of 20 ul of internal standard mixture ($^{13}C_6$, $d_7$-Glucose, $^{13}C_{12}$-sucrose and $d_2$-Fructose solution as 20 ug/mL concentration, respectively in water). Finally, 460 ul of water will be added to the vial. 20 ul will be injected onto LC/MS.

HPLC/MS/MS Analysis

Separation will be made by UPLC (Aquity UPLC™ system, Waters) using Aquity UPLC BEH Amide column (2.1×50 mm, 1.7 μm). Identification and quantification will be made by Q trap 4000 (a hybrid triple quadrupole/linear ion trap mass spectrometer, Applied Biosystems). Sugar compounds will be eluted with a gradient of solvent A (90% Acetonitrile/10% water/0.1% $NH_4OH$) and solvent B (0.1% $NH_4OH$) set according to the following program: 0 min, 0% B; 1.7 min, 10% B; 4 min, 25% B; 4.1 min, 80% B; 5.1 min, 80% B; 5.2 min, 0% B. The solvent flow rate will be set to 0.2 ml. The column heater will be set to 25° C. The eluents will be monitored by a Q trap 4000. MS conditions will be as follows: ESI spray ion voltage, +4500 V; curtain gas, 20 arb; Gas1,30 arb; Gas2, 40 arb; capillary temperature, 550° C.; cad gas, medium; entrance potential, −10 V. The MRM (multiple reaction monitoring) mode will be used to identify and quantitate both labeled and nonlabeled sugar compounds in the conditions described with dwell time as 100 ms. Collision energy optimized for each sugar compound will be applied. Data will be processed by Analyts (Ver 5) software.

Example 6: Measurement of Cytokinin Levels

Cytokinin levels will also be measured such as by the following protocol. Fresh leaves (0.2 g) are ground to a fine powder in liquid N2 and extracted with precold 80% methanol at 4 C overnight. The supernatant is collected after centrifugation at 3000 g for 10 min. The pellet is re-extracted with 80% methanol. The two supernatant fractions are combined and dried in vacuum and resolved in NH4Ac (0.1M, pH9.0). After passing through a C18 Sep-pak column, the eluted solution is dried and dissolved in water. The samples are then subjected to reverse-phase C18 HPLC/6520 Accurate-Mass Q-TOF LC/MS analysis (Agilent Technologies) and the UV absorbance is monitored at 269 nm. Analysis will be repeated with at least three different samples.

Example 7. Methods for Measuring Delayed Leaf Senescence

The following procedure is used for all assays described in this example. Topically treated *Zea mays* plants will be monitored for yellowing of leaves and will be visually assessed at approximately 40 days after pollination. The percentage of each leaf that has turned yellow will be recorded. Leaves are sampled using a hole punch, and chlorophyll will be extracted and quantified using the following method. Each leaf disc is placed in a microcentrifuge tube and 1 ml of ice-cold 80% acetone is added. The tissue is then ground with a blue pestle with sand, until it is completely disintegrated. The tube is centrifuged in a microcentrifuge for 5 minutes at maximum speed at 4° C. The supernatant is removed and absorbance is measured in a spectrophotometer in a 1 ml glass cuvette at 663.2 nm, 646.8 nm and 710 nm. Chlorophyll a and b concentrations (μg/ml) are calculated using the following equations:

$$Chl_a=12.25*(A_{663.2}-A_{710})-2.79*(A_{646.8}-A_{710})$$

$$Chlb=21.5*(A_{646.8}-A_{710})-5.1*(A_{663.2}-A_{710})$$

Leaves of plants treated with trigger molecules of Table 2 and the incorporated sequence listing will have a higher percentage of green leaf area and more chlorophyll per leaf weight compared with plants treated with non-efficacious control polynucleotides. Photosynthesis of comparable leaves of each of these plants will be measured using a LiCor photosynthesis system (LiCor Biosciences) or PAM fluorescence monitor (Heinz Walz GmbH) following the manufacturer's recommended procedures. Leaves of plants treated with efficacious polynucleotides will have a higher rate of photosynthesis compared to leaves of plants treated with non-efficacious control polynucleotides.

Chlorophyll will be extracted from leaves one week after topical treatment using a hole punch on treated leaves or leaves from above the treatment site. Leaf discs are placed on 3 layers of wet Whatman No. 1 filter paper and placed in the dark at 25° C. One week after sampling, chlorophyll is extracted from the leaf pieces and measured spectrophotometrically using the method described above. Leaf pieces from plants treated with efficacious polynucleotides will have a higher concentration of chlorophyll compared with leaf pieces from plants treated with non-efficacious control polynucleotides.

To determine if the delays in senescence, observed in topically suppressed INVINH1 lines impacted yield, the weight of seeds and/or fruits will be measured and compared to null lines. Other growth parameters correlated to yield, such as plant height, fresh and dry weight, biomass, PS efficiency will also be measured.

Example 8. Invertase Inhibitor Sugar Analysis

The following example describes the application a 250 bp dsRNA section of the Invertase Inhibitor ORF from tomato SEQ ID NO: 9 to tomato leaves. Invertase Inhibitor (INVI) is a single gene in tomato. The selection of the 250 bp molecule was done by dsRNA Designer. SEQ ID NO 65: is a fragment of DNA (bp 266-516 of SEQ ID NO: 9) that contained T7 promoter regions on both sense and antisense strands for in vitro transcription of the RNA. Primer sequences SEQ ID NO: 66 and SEQ ID NO: 67 were used for cloning SEQ ID NO: 65 and contain T7 RNA polymerase transcription start sites.

T7 RNA Synthesis:

RNA synthesis was performed for 3 hrs at 37° C. 50U RNAse free DNase (Ambion) was added and incubation continued for an additional 20 minutes. The samples were heated to 75° C. for 15 minutes in a heating block and allowed to cool for 2.5 hours by turning off the unit and keeping the samples in the block. Tubes were then transferred to ice and 5 µL of diluted RNAse A was added. After additional incubation for 1 hr on ice the samples were applied to a S-400 Spinc column (GE Healthcare). The RNA was quantitated using a nanodrop (Factor 45 used for conversion), then stored at −20° C. until applied to tomato leaves.

Topical Application of SEQ ID NO 65 to Tomato:

Tomato plants (HP375 cultivar) at the 2-leaf stage (2 cotyledons and 2 true leaves) were grown in a peat moss, composted bark and perlite soil mix. Plants were grown in a 14/10 hr light/dark cycle at 22° C. constant temperature. Five plants were used per treatment. All plants, except untreated were sprayed with an airbrush using a solution of 0.1% Silwet L-77 until the surface became moist. Triggers were prepared directly at the application site by diluting 2× trigger buffer into aliquots of diluted dsRNA. Approximately 200 µL of trigger solution was sprayed to the surface of each plant in a treatment (equaling 0.025 pmol/ml or 25 pmol/ml).

The formulation of the dsRNA nucleotide solution is: 0.6 ng/µL dsRNA in a 200 µL solution of trigger buffer containing 200 mM NaPO4, 25% Ammonium Sulfate, 0.01% Silwet L-77 in water.

Controls used in this experiment were untreated plants, buffer treated or treated with a 184 bp dsRNA fragment (SEQ ID NO: 68) of Green Fluorescent Protein (GFP). Fourteen days after treatment expanded leaves were collected and immediately snap frozen in liquid N2. Ground tissue was used for sugar analysis.

TABLE 6

Results of the total sugar analysis.

| Sample Number | Customer_ID | Rep_1 | Fructose (ppm) | Glucose (ppm) | Sucrose (ppm) |
|---|---|---|---|---|---|
| 01 | 01 Untreated | 1 | 4392.37 | 3171.70 | 8477.55 |
| 02 | 02 Untreated | 1 | 3352.82 | 2921.07 | 14979.87 |
| 03 | 03 Untreated | 1 | 2515.35 | 2348.25 | 16236.25 |
| 04 | 04 Untreated | 1 | 2304.13 | 2016.18 | 14624.43 |
| 05 | 05 Untreated | 1 | 1166.54 | 1025.38 | 15539.74 |
| 06 | 06 Buffer Only | 1 | 3589.60 | 3046.86 | 14809.14 |
| 07 | 07 Buffer Only | 1 | 1488.87 | 971.70 | 12871.35 |
| 08 | 08 Buffer Only | 1 | 2272.74 | 1845.75 | 10155.17 |
| 09 | 09 Buffer Only | 1 | 1805.06 | 1409.68 | 10474.74 |
| 10 | 10 Buffer Only | 1 | 2755.10 | 2509.81 | 10850.00 |
| 11 | 11 GFP dsRNA 5 pmol | 1 | 1868.44 | 1225.99 | 12715.25 |
| 12 | 12 GFP dsRNA 5 pmol | 1 | 1614.75 | 1331.54 | 11859.06 |
| 13 | 13 GFP dsRNA 5 pmol | 1 | 2083.46 | 1176.95 | 17706.78 |
| 14 | 14 GFP dsRNA 5 pmol | 1 | 2082.59 | 1080.25 | 12704.30 |
| 15 | 15 GFP dsRNA 5 pmol | 1 | 961.24 | 458.47 | 14317.11 |
| 16 | 16 INVI dsRNA 5 pmol | 1 | 4097.93 | 2960.00 | 11920.00 |
| 17 | 17 INVI dsRNA 5 pmol | 1 | 1408.23 | 801.75 | 12017.81 |
| 18 | 18 INVI dsRNA 5 pmol | 1 | 516.79 | 246.46 | 7432.30 |
| 19 | 19 INVI dsRNA 5 pmol | 1 | 636.80 | 261.34 | 9888.61 |
| 20 | 20 INVI dsRNA 5 pmol | 1 | 1860.80 | 1119.70 | 7819.40 |

FIG. 1 is a graph of sugar analysis wherein the amount of sugars (fructose, glucose, and sucrose) measured in untreated, buffer treated, GFP dsRNA treated, and INVI dsRNA treated plants are shown in comparison to one another.

LITERATURE CITED

Balibrea Lara, M. E., M.-C. Gonzalez Garcia, et al. (2004). "Extracellular Invertase Is an Essential Component of Cytokinin-Mediated Delay of Senescence." *The Plant Cell Online* 16(5): 1276-1287.

Gan, S. and R. M. Amasino (1995) "Inhibition of Leaf Senescence by Autoregulated Production of Cytokinin." *Science* 270(5244): 1986-1988.

Hajirezaei, M. R., Y. Takahata, et al. (2000). "Impact of elevated cytosolic and apoplastic invertase activity on carbon metabolism during potato tuber development." *Journal of Experimental Botany* 51(suppl 1): 439-445.

Jin, Y., D.-A. Ni, et al. (2009). "Posttranslational Elevation of Cell Wall Invertase Activity by Silencing Its Inhibitor in Tomato Delays Leaf Senescence and Increases Seed Weight and Fruit Hexose Level." *The Plant Cell Online* 21(7): 2072-2089

Kambiranda, D., H. Vasanthaiah, et al. (2011). "RELATIONSHIP BETWEEN ACID INVERTASE ACTIVITY AND SUGAR CONTENT IN GRAPE SPECIES." *Journal of Food Biochemistry:* 1745-4514.

Liu, L., Y. Zhou, et al. (2010). "Identification and Application of a Rice Senescence-Associated Promoter." *Plant Physiology* 153(3): 1239-1249.

Mounet, F., A. Moing, et al. (2009). "Gene and Metabolite Regulatory Network Analysis of Early Developing Fruit Tissues Highlights New Candidate Genes for the Control of Tomato Fruit Composition and Development." *Plant Physiology* 149(3): 1505-1528.

Nookaraju, A., C. P. Upadhyaya, et al. (2010). "Molecular approaches for enhancing sweetness in fruits and vegetables." *Scientia Horticulturae* 127(1): 1-15.

Robson, P. R. H., I. S. Donnison, et al. (2004). "Leaf senescence is delayed in maize expressing the *Agrobacterium* IPT gene under the control of a novel maize senescence-enhanced promoter." *Plant Biotechnology Journal* 2(2): 101-112.

Roitsch, T., M. E. Balibrea, et al. (2003). "Extracellular invertase: key metabolic enzyme and PR protein." *Journal of Experimental Botany* 54(382): 513-524.

Roitsch, T. and M.-C. González (2004). "Function and regulation of plant invertases: sweet sensations." *Trends in Plant Science* 9(12): 606-613.

Ruan, Y.-L., D. J. Llewellyn, et al. (2003). "Suppression of Sucrose Synthase Gene Expression Represses Cotton Fiber Cell Initiation, Elongation, and Seed Development." *The Plant Cell Online* 15(4): 952-964.

Tang, G.-Q., M. Lüscher, et al. (1999). "Antisense Repression of Vacuolar and Cell Wall Invertase in Transgenic Carrot Alters Early Plant Development and Sucrose Partitioning." *The Plant Cell Online* 11(2): 177-190.

Tomlinson, K. L., S. McHugh, et al. (2004). "Evidence that the hexose-to-sucrose ratio does not control the switch to storage product accumulation in oilseeds: analysis of tobacco seed development and effects of overexpressing apoplastic invertase." *Journal of Experimental Botany* 55(406): 2291-2303.

What is claimed is:

1. A method for producing a tomato plant exhibiting increased invertase activity, the method comprising topically applying to a tomato plant surface a composition that comprises:
   a. at least one double-stranded RNA (dsRNA) polynucleotide that comprises at least 18 contiguous nucleotides that are identical or complementary to a tomato INVINH1 gene transcript, wherein the dsRNA polynucleotide is not operably linked to a promoter or to a viral vector; and
   b. a transfer agent comprising a surfactant comprising an organosilicone preparation that conditions the tomato plant surface to permeation by the dsRNA polynucleotide into cells of the tomato plant; wherein said tomato plant exhibits increased invertase activity in comparison to a control tomato plant that has not been treated with a composition comprising a polynucleotide and a transfer agent and wherein the increased invertase activity results from suppression of said tomato INVINH1 gene.

2. The method of claim 1, wherein said dsRNA polynucleotide comprises at least 18 contiguous nucleotides that are identical or complementary to SEQ ID NO: 9.

3. The method of claim 2, wherein one strand of said dsRNA polynucleotide molecule is complementary to a sequence selected from the group consisting of SEQ ID NOs: 41, 42, and 65.

4. The method of claim 1, wherein said composition further comprises one or more additional dsRNA polynucleotides that are essentially identical or complementary to a different target gene or transcript thereof.

5. The method of claim 1, wherein said dsRNA polynucleotide is at least 18 to about 24, about 25 to about 50, about 51 to about 100, about 101 to about 300, about 301 to about 500, or at least about 500 or more residues in length.

6. The method of claim 1, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

7. The method of claim 1, wherein said composition further comprises a non-polynucleotide herbicidal molecule and said tomato plant is resistant to said herbicidal molecule.

* * * * *

SEQUENCE LISTING

```
<160> NUMBER OF SEQ ID NOS: 68

<210> SEQ ID NO 1
<211> LENGTH: 444
<212> TYPE: DNA
<213> ORGANISM: Capsicum

<400> SEQUENCE: 1
gtagaaacaa catgtaagaa cacaccaaat tatgaactat gtgtgaagac tttggtttca      60
gacaaaagaa gtggaaatgg agacataaca acattggcat taataatggt ggatgctatt     120
aaatcaaaag cttatgaagc tgctattact atttctaaac ttagaagatc taatccccct     180
caagcttgga aacttccctt gaaaaattgt gccttttcat ataaggtaat tctaacagca     240
agtatgccag aagcaataga agcattaaca aaaggtgatc caaaatttgc agaagatgga     300
atggtaggtt catctggtga tgcacaagaa tgtgaaggtt atttcaaagc tactacaaat     360
aaatactcac cacttactaa attaaatgtt gctgttcatg atctttctga tgttggtaga     420
gctattgtca gaaatttatt atga                                            444

<210> SEQ ID NO 2
<211> LENGTH: 549
<212> TYPE: DNA
<213> ORGANISM: Glycine

<400> SEQUENCE: 2
atgaaaatta tggaatcatt agctcttatc ttctacagta ctcttgtttt agctacgatt      60
tcagttccag caactaactc cagaatcatc catcaaaaaa acaatgccaa tctgattgaa     120
gaaacttgca agcagacacc ccatcacgac ctttgcatcc aatacctctc ctccgaccct     180
cgcagcaccg aagcagatgt gacagggctg gcacttatta tggtcaacgt aatcaaaatc     240
aaagcaaaca atgcattgga caaatccac caactgcttc agaaaaaccc tgaacctagt     300
caaaaggaac cactgagttc gtgtgctgct agatacaaag caattgtgga agctgacgtg     360
gcacaagccg ttgcgtctct gcagaaagga gacccaagt tcgcagaaga tggtgccaat     420
gatgctgcta ttgaggccac cacttgtgag aacagcttct ctgctgggaa atcgccactc     480
accaatcaca acaatgctat gcacgatgtt gcaaccataa ctgcagctat agttagacaa     540
ttgctctag                                                             549

<210> SEQ ID NO 3
<211> LENGTH: 555
<212> TYPE: DNA
<213> ORGANISM: Glycine

<400> SEQUENCE: 3
atgacaaact tgaagtctct aattctcttc ttttatctcc tagccattgt tgttatgatt      60
tcaataccat caagccactg cagcagaacc ttgcttccag aaaacgaaaa gctgatagag     120
aacacttgca agaaaactcc caactacaac gtttgccttg agtctctgaa ggcaagccct     180
```

-continued

| | |
|---|---|
| gggagctcca gtgctgacgt cacagggctg gctcaaatca tggtcaaaga gatgaaggcc | 240 |
| aaagcaaacg atgcattgaa aagaatccaa gagttgcaga gggtgggagc atcggggcct | 300 |
| aagcaaagaa gagccttgag ttcttgtgct gataaataca aagcggtttt aattgctgat | 360 |
| gttccacaag ccactgaggc tctgcagaaa ggtgacccca gtttgctga agatggggct | 420 |
| aatgatgctg ctaatgaggc tacttattgt gagactgatt tctctgcagc agggaattcc | 480 |
| ccactcacca aacagaacaa tgctatgcat gatgttgctg ctgttactgc cgctattgtt | 540 |
| agattgttgc tctaa | 555 |

<210> SEQ ID NO 4
<211> LENGTH: 1500
<212> TYPE: DNA
<213> ORGANISM: Glycine

<400> SEQUENCE: 4

| | |
|---|---|
| attatagcat ctattgggca gagtgatcac ttggtcattc taaagagaca ggagtacacg | 60 |
| cctgaagaag ctttcacact ggccttctag ctagttagtt aattatgtgc gtggcctccc | 120 |
| ccccttttt ttttgtcttt ttaaatgtgc agcagcattt tttacagtta tacgatttac | 180 |
| attagccctt aattaccaat atggtattga atgattgaga gataatgatg ctcttgaata | 240 |
| tatggtaagg gatttaatcg tgtatatgca agaatgctaa gagaaataaa ctacttaata | 300 |
| ttttttcaac ttccaaaaat aagtctctaa ttctcaataa aagtatatag gctctgagaa | 360 |
| aatttcatca ttaaccatat acgcaagtca taacatggtc cggtcagata ttttatgcaa | 420 |
| aaaaaaaaa ttattaaata atttaagatt atcacattag ttggacttag atctcaatca | 480 |
| ataatcatgc cacacattat tatcttaaga acatgcttgc tcactaactt gaaggtttgt | 540 |
| aacgtttata taaatcaatt attttaaaat ttaaaatata aactaattta gtcaataatt | 600 |
| tagttcaact tcatgttgaa ataactgaat tattacaaag ttggcagatt caatgattaa | 660 |
| gtttatataa aaggactaat ttcctttaaa aaaagactaa tttatgaatg atagacgaag | 720 |
| ttgataaatt tgaagactaa attataccac acaaattttt tgagattaat ttacttaata | 780 |
| ttatttggtt tattattttt taaattatgt gaagattata aaaataata agttaaaaat | 840 |
| atacaacaaa caaatatca cctacaattt tataattttg ataaagtgt aaaaatccct | 900 |
| ctaacggaat ggactatagt acatcgtttg aatgcaaatt tgagcctaac atctactttt | 960 |
| tcattgtttt tattattatt ttttaaaaaa aaatcattga ttaataatga aagataaata | 1020 |
| aaaagttaaa ttatactgca ctgttttgt ttgagaatta aatatgcact acatttttaat | 1080 |
| ttagtgtgaa tggattttta aggatggttt ttttcttctc aatataattc ttagcattat | 1140 |
| tgcaattag ttttatcaa ctaggaattt tcagaagatg atacaatact tttgagttaa | 1200 |
| gttttaaagt atacagtaaa ggtaagaatt tcacataatt tttaatcgta taaagatata | 1260 |
| tatatattgt tcttttttct tcttctagaa aatggtacga ttaactaaaa taaatgcatg | 1320 |
| ttctctgtgc cgaaagctga cccacgacca tgatcagttt cgtgcacgac acaatctctg | 1380 |
| gcacagcttc ttaactataa aatgtctcag caattttcag ttctgaaaag acattgagtg | 1440 |
| ttccatccat cccttcttca tcttctactt ctatctccct acatactcat tcaaacagac | 1500 |

<210> SEQ ID NO 5
<211> LENGTH: 1500
<212> TYPE: DNA
<213> ORGANISM: Glycine

```
<400> SEQUENCE: 5
aattaattac tcatagaact ttgtaactat aaatattata ccaaccaact ttattcgtac      60
ctacccgtgt atatttatta tattttataa cttttttaagt taaaaaatac ttgtaacact     120
ttacaattaa aaattatatt tgtttttact attttcttcg ttcaagttac atttaattca     180
tttaatttaa ttaatatttta ttcattcatt tatttatttt tcatcattaa tatttgacct    240
aaatatattt ttaattccta taaaatgact aaatttgat tttgatgttt tgtttttttc      300
ttcttcttta atttggtttt catctccaaa aaagtgagat aattgttcat aacaaacagc     360
agtcctcttt ttttttaaca tatctttaaa tttcacctttt ttttataaaa taacataaat    420
tccatacata tttaataaaa tttattttcac tattacattg acattacagt ttatgtaaaa    480
aaaaatacac aaaaaaaagt aaaacagttt atgtatcttt gtaatgaaat cttattaaat     540
gtttgaatag atattttatt ttttattaaa aaattatggt tgaaagcttg gatatcatta     600
actcaaaata taataattta tattagatat aacagatcga gatcaacctg ataacgtgat     660
tcctcagtcc aatatatatt tttccggata aataaaggcc caattggcaa tggcatgtat     720
taccttaatg caaccatgta ttactacttg catcagatag agatagagta cgagccaata    780
attgattaca tgcaaataca gccgcaaatt aacatcacga acaattttaa ttaaatacct    840
tcttttgtgc ataaaataa ttaagatata tatagtggaa gaaaaagacc acacagtgaa     900
tttgggtaat ctaaattaaa gattatttta aaataaaaag gtaaagtcat aattttttaat   960
taaaattaat aacaaaaata cgcataaata tataaaatat ttaagtcatt caatattatt   1020
tttcaattaa taattataat ttttatgttt ctaaatgca ttcaaattcg atggacatct    1080
actttaattt caaacaaatt agtctaggaa gatcttgtc gtaagtcatg attgaatttg    1140
caattttaac cgcaacaaat taaaaatttg tcaagccaac atataacggt ggatatttaa    1200
gcacagaaag caagctggaa tggagacaac aattttataa gatgatagtt gcacacttttt   1260
ttgcttaaaa agttatattg ttatatatat aaaaagttgg tttgaaaaaa ccaccatgta    1320
tgtggaaaat tgcgtacata tatcaatctt cgataacatt cttcttacat atatctgcat    1380
ttaaatagga aaaaggttag gtccactaca tctgctccta accataaaaa ggcctagcag    1440
cattccattc agtggaatct agcaactacc aaaaccaatc tctttcaata atcaacaaca    1500

<210> SEQ ID NO 6
<211> LENGTH: 399
<212> TYPE: DNA
<213> ORGANISM: Unknown
<220> FEATURE:
<223> OTHER INFORMATION: Sequence listing for 58654.

<400> SEQUENCE: 6
atgaagaatt tgattttcct aatgatgttt ctgatcatat tactacaaac aaacgccaat      60
aatctagtag aaactacatg caaaaacaca ccaaattatc aactttgtct gaaaactctg     120
ctttcggaca aacgaagtgc aacaggggat attacaacgt tggcactaat tatggtcgat    180
gctataaaat ctaaggctaa tcaagctgca ctcacaattt caaaactccg gcattctaat    240
cctccagcag cttggaaagg tcctttgaaa aattgtgctt tttcatataa ggtaattttta    300
acagcaagtt tgcctgaagc aattgaagct ttaacaaaag gggatccaaa atttgctgaa    360
gatggaatgg taggttcatc tggagatgca caagaatgt                           399

<210> SEQ ID NO 7
<211> LENGTH: 501
```

<212> TYPE: DNA
<213> ORGANISM: Nicotiana

<400> SEQUENCE: 7

```
atgaagaatt tgattttcct aacgatgttt ctgactatat tactacaaac aaacgccaat     60
aatctagtag aaactacatg caaaaacaca ccaaattacc aactttgtct gaaaactctg    120
ctttcggaca acgaagtgc aacaggggat atcacaacgt tggcactaat tatggtcgat     180
gcaataaaag ctaaagctaa tcaggctgca gtgacaattt cgaaactccg gcattcgaat    240
cccctgcag cttggaaagg tcctttgaaa aactgtgcct tttcatataa ggtaattta      300
acagcaagtt tgcctgaagc aattgaagca ttgacaaaag gagatccaaa atttgctgaa    360
gatggaatgg taggttcatc tggagatgca caagaatgtg aggagtattt caagggtagt    420
aaatcaccat tttctgcatt aaatatagca gttcatgaac tttctgatgt tgggagagct    480
attgtcagaa atttattgtg a                                              501
```

<210> SEQ ID NO 8
<211> LENGTH: 519
<212> TYPE: DNA
<213> ORGANISM: Nicotiana

<400> SEQUENCE: 8

```
atgagaaact tattccccat atttatgtta atcaccaatc tagcattcaa cgacaacaac     60
aacagtaata atatcatcaa cacgacctgc agagccacca caaactaccc cttgtgcctc    120
accaccctcc actctgatcc ccgtacctcc gaggccgagg gggcggacct caccaccctc    180
ggcctcgtca tggtagatgc ggtaaaatta aagtccatcg aaataatgaa agtataaaa     240
aaactcgaaa atcgaaccc cgagttgaga ctacctctta gccaatgtta catagtgtat    300
tatgctgttc tacatgctga tgtaactgtt gctgttgaag ctttaaaaag aggagtccct    360
aaatttgctg aaaatggaat ggttgatgtt gctgtagaag cagaaacttg tgagtttagt    420
tttaagtata atggattggt ttctccagtt tctgatatga ataaggagat tattgaactg    480
tcttctgtgg ctaaatctat tattagaatg ctattatga                           519
```

<210> SEQ ID NO 9
<211> LENGTH: 516
<212> TYPE: DNA
<213> ORGANISM: Solanum

<400> SEQUENCE: 9

```
atgaaaattt tgattttcct aataatgttt cttgctatgt tgctagtaac aagtgggaat     60
aataatctag tagagacaac atgcaagaac acaccaaatt ataatttgtg tgtgaaaact    120
ttgtctttag acaaaagaag tgaaaaagca ggagatatta caacattagc attaattatg    180
gttgatgcta ttaaatctaa agctaatcaa gctgctaata ctatttcaaa acttaggcat    240
tctaatcctc ctcaagcttg gaaagatcct ttgaagaatt gtgcctttt cgtataaggta    300
attttaccag caagtatgcc agaagcatta gaagcattaa caaaaggtga tccaaaattt    360
gcagaagatg gaatggttgg ttcttctggt gatgcacaag aatgtgaaga atattttaaa    420
gctacaacta ttaaatattc accacttct aaattaaata tagatgttca tgaactttct    480
gatgttggta gagccattgt aagaaattta ttgtaa                              516
```

<210> SEQ ID NO 10
<211> LENGTH: 1500
<212> TYPE: DNA

<213> ORGANISM: Solanum

<400> SEQUENCE: 10

```
taattatgat ctcaaattat taattctaat tacaacaata aatacatatc taataaaatt    60
taaaataaat ataaaattta aattaaaatt attaaatcgt aattaatact ctagctccag   120
aaaccaatca tgcaaatggt tccaaggaat caacccaaaa agaaagagat aagagaaagg   180
cataataaag tgatgcattc cactttcaca aggataatga aaggaaccat tatctctaag   240
aattataaat gttaactaca ctaataacat tacaattgta attatattta tatattaaaa   300
tatactaatt attatataca tttatctttt aggctatatt atcattaaat taaaaaatat   360
attataaata taaagttatt cattttttttc ttttattata taaaatttat ctgaaattat   420
atatacacat gcatcatttt ttttaaaaaa aattaattct acttaattca ttttttaatt   480
attaatatca tataactgtc caaaaattat tgctcatatg atgcctcaca aatcatgctt   540
tgtctttttc caagtgtaaa aagggaggtg caataatgca ttttggtttg tatacatttt   600
gtagtttcaa agtcttatca tattgagaatc atagaattaa tgagtagtat gatttaatta   660
tctaaggctt gtttggtagt tagttagaaa ctaaatcatt caattgtatt ataaatgata   720
tgattagcat tagagaggat aaaattatcc aataaaatta catttttattt aagtttaaat   780
taattattta tctgtttatt tattaattta atttaattca attcgattga ttttacaaat   840
agccttaaaa agattgattt agaatttcga atctcgttta acaaactcat taaataaatt   900
gcttcatctt taaaaaaatt gttaaacata agtatgaatt gattttttcta cttataaagc   960
agatgttcag aatatttcaa gataataaac ttattcaatt aattataagt tacgtaaaaa  1020
ataaaatcta acgataataa attaaataat attttatttg aacatcggaa tttatggtcg  1080
cgagcgaagc tagtaagcat ctcggaattc tttctaaacc tctttcaaaa ttaaaatata  1140
tagtctcttc gatttcttca tatatgtacc tcatgtttcg aatgaatttt aatgaaaatt  1200
ttaattctgt ccttcgaact gactactcta gagactatcc ccaggtccaa acaaacccac  1260
gaaaaacaga ttcaacgaaa attctgattc cgtccctaaa ccttactacc ctagaaacta  1320
caaccccccc cccccccccc aacaaggccc aaacaaaccc caccgaaaac acaaagcaag  1380
agatgattaa cacgcaattg aatccatcca tttactatat aaaaaaacat acacacacac  1440
actatactcc atacaaagaa aatccacatt tagttttaaa ttttcccaaa aatttcaaaa  1500
```

<210> SEQ ID NO 11
<211> LENGTH: 510
<212> TYPE: DNA
<213> ORGANISM: Vitis

<400> SEQUENCE: 11

```
atgagatcat ctgtgtttct cctgtgtgta atgggtcttt ctctgaccca aatcgaattc    60
tccacttcag atttggtaaa gcaaacatgc aagcatacac ccaactacga tctctgtgtg   120
aagactctgc tctcagaccc acgaagctct cacgcagacg tcgcaggttt ggccatggtg   180
atggtggacg tgatcaaggc caaaacaatc gccaccctcc acagaatcag cgaattgctg   240
ggcacaaccc gatacccaaa aacgaaggct gccttgaggc gttgtgtaga gttgtatgat   300
aatgcagttt tgaaggctga tcttccatca gcgatgcaag ctctcaagac tggtgttccc   360
aaatttgcag aagaaggtac taatgatgct gctaacgagg ccgactcctg cgagagaacc   420
ttcagtgggg catcccccat tacctctttc aataggtatg tcagtgacct ctgtcgtgtg   480
gcttctgcca ttatcaggct cttgttgtga                                    510
```

```
<210> SEQ ID NO 12
<211> LENGTH: 201
<212> TYPE: DNA
<213> ORGANISM: Capsicum

<400> SEQUENCE: 12
gtagaaacaa catgtaagaa cacaccaaat tatgaactat gtgtgaagac tttggtttca      60
gacaaaagaa gtggaaatgg agacataaca acattggcat taataatggt ggatgctatt     120
aaatcaaaag cttatgaagc tgctattact atttctaaac ttagaagatc taatccccct     180
caagcttgga aacttcccct g                                                201

<210> SEQ ID NO 13
<211> LENGTH: 201
<212> TYPE: DNA
<213> ORGANISM: Capsicum

<400> SEQUENCE: 13
cccctcaagc ttggaaactt cccttgaaaa attgtgcctt tcatataag gtaattctaa       60 cagcaagtat gccagaagca atagaagcat taacaaaagg tgatccaaaa tttgcagaag     120
atggaatggt aggttcatct ggtgatgcac aagaatgtga aggttatttc aaagctacta     180
caaataaata ctcaccactt a                                                201

<210> SEQ ID NO 14
<211> LENGTH: 201
<212> TYPE: DNA
<213> ORGANISM: Glycine

<400> SEQUENCE: 14
atgaaaatta tggaatcatt agctcttatc ttctacagta ctcttgtttt agctacgatt      60
tcagttccag caactaactc cagaatcatc catcaaaaaa acaatgccaa tctgattgaa     120
gaaacttgca agcagacacc ccatcacgac ctttgcatcc aatacctctc ctccgaccct     180
cgcagcaccg aagcagatgt g                                                201

<210> SEQ ID NO 15
<211> LENGTH: 201
<212> TYPE: DNA
<213> ORGANISM: Glycine

<400> SEQUENCE: 15
accctcgcag caccgaagca gatgtgacag ggctggcact tattatggtc aacgtaatca      60
aaatcaaagc aaacaatgca ttggacaaaa tccaccaact gcttcagaaa aaccctgaac     120
ctagtcaaaa ggaaccactg agttcgtgtg ctgctagata caaagcaatt gtggaagctg     180
acgtggcaca agccgttgcg t                                                201

<210> SEQ ID NO 16
<211> LENGTH: 201
<212> TYPE: DNA
<213> ORGANISM: Glycine

<400> SEQUENCE: 16 atgacaaaact tgaagtctct aattctcttc ttttatctcc tagccattgt tgttatgatt     60
tcaataccat caagccactg cagcagaacc ttgcttccag aaaacgaaaa gctgatagag     120
aacacttgca agaaaactcc caactacaac gtttgccttg agtctctgaa ggcaagccct     180
```

```
gggagctcca gtgctgacgt c                                              201
```

<210> SEQ ID NO 17
<211> LENGTH: 201
<212> TYPE: DNA
<213> ORGANISM: Glycine

<400> SEQUENCE: 17

```
gccctgggag ctccagtgct gacgtcacag ggctggctca aatcatggtc aaagagatga    60
aggccaaagc aaacgatgca ttgaaaagaa tccaagagtt gcagagggtg ggagcatcgg   120
ggcctaagca agaagagcc ttgagttctt gtgctgataa atacaaagcg gttttaattg    180
ctgatgttcc acaagccact g                                             201
```

<210> SEQ ID NO 18
<211> LENGTH: 201
<212> TYPE: DNA
<213> ORGANISM: Glycine

<400> SEQUENCE: 18

```
aattgctgat gttccacaag ccactgaggc tctgcagaaa ggtgacccca agtttgctga    60
agatggggct aatgatgctg ctaatgaggc tacttattgt gagactgatt ctctgcagc   120
agggaattcc ccactcacca aacagaacaa tgctatgcat gatgttgctg ctgttactgc   180
cgctattgtt agattgttgc t                                             201
```

<210> SEQ ID NO 19
<211> LENGTH: 201
<212> TYPE: DNA
<213> ORGANISM: Glycine

<400> SEQUENCE: 19

```
attatagcat ctattgggca gagtgatcac ttggtcattc taaagagaca ggagtacacg    60
cctgaagaag ctttcacact ggccttctag ctagttagtt aattatgtgc gtggcctccc   120
cccctttttt ttttgtcttt ttaaatgtgc agcagcattt tttacagtta tacgatttac   180
attagccctt aattaccaat a                                             201
```

<210> SEQ ID NO 20
<211> LENGTH: 201
<212> TYPE: DNA
<213> ORGANISM: Glycine

<400> SEQUENCE: 20

```
tttacattag cccttaatta ccaatatggt attgaatgat tgagagataa tgatgctctt    60
gaatatatgg taagggattt aatcgtgtat atgcaagaat gctaagagaa ataaactact   120
taatatttt tcaacttcca aaaataagtc tctaattctc aataaaagta tataggctct    180
gagaaaattt catcattaac c                                             201
```

<210> SEQ ID NO 21
<211> LENGTH: 201
<212> TYPE: DNA
<213> ORGANISM: Glycine

<400> SEQUENCE: 21

```
gctctgagaa aatttcatca ttaaccatat acgcaagtca taacatggtc cggtcagata    60
ttttatgcaa aaaaaaaaaa ttattaaata atttaagatt atcacattag ttggacttag   120
atctcaatca ataatcatgc cacacattat tatcttaaga acatgcttgc tcactaactt   180
```

```
gaaggtttgt aacgtttata t                                             201
```

<210> SEQ ID NO 22
<211> LENGTH: 201
<212> TYPE: DNA
<213> ORGANISM: Glycine

<400> SEQUENCE: 22

```
aacttgaagg tttgtaacgt ttatataaat caattatttt aaaatttaaa atataaacta    60
atttagtcaa taatttagtt caacttcatg ttgaaataac tgaattatta caaagttggc   120
agattcaatg attaagttta tataaaagga ctaatttcct ttaaaaaaag actaatttat   180
gaatgataga cgaagttgat a                                             201
```

<210> SEQ ID NO 23
<211> LENGTH: 201
<212> TYPE: DNA
<213> ORGANISM: Glycine

<400> SEQUENCE: 23

```
tttatgaatg atagacgaag ttgataaatt tgaagactaa attataccac acaaattttt    60
tgagattaat ttacttaata ttatttggtt tattattttt taaattatgt gaagattata   120
aaaataata agttaaaaat atacaacaaa caaatatca cctacaattt tataattttg    180
ataaagtgt aaaaatccct c                                              201
```

<210> SEQ ID NO 24
<211> LENGTH: 201
<212> TYPE: DNA
<213> ORGANISM: Glycine

<400> SEQUENCE: 24

```
ttttgataaa agtgtaaaaa tccctctaac ggaatggact atagtacatc gtttgaatgc    60
aaatttgagc ctaacatcta cttttttcatt gtttttatta ttatttttta aaaaaaaatc   120
attgattaat aatgaaagat aaataaaaag ttaaattata ctgcactgtt tttgtttgag   180
aattaaatat gcactacatt t                                             201
```

<210> SEQ ID NO 25
<211> LENGTH: 201
<212> TYPE: DNA
<213> ORGANISM: Glycine

<400> SEQUENCE: 25

```
ttgagaatta aatatgcact acattttaat ttagtgtgaa tggattttta aggatggttt    60
ttttcttctc aatataattc ttagcattat tggcaattag ttttatcaa ctaggaatt    120
tcagaagatg atacaatact tttgagttaa gttttaaagt atacagtaaa ggtaagaatt   180
tcacataatt tttaatcgta t                                             201
```

<210> SEQ ID NO 26
<211> LENGTH: 201
<212> TYPE: DNA
<213> ORGANISM: Glycine

<400> SEQUENCE: 26

```
gaatttcaca taattttaa tcgtataaag atatatatat attgttcttt tttcttcttc     60
tagaaaatgg tacgattaac taaaataaat gcatgttctc tgtgccgaaa gctgacccac   120
```

```
gaccatgatc agtttcgtgc acgacacaat ctctggcaca gcttcttaac tataaaatgt    180
ctcagcaatt ttcagttctg a                                             201

<210> SEQ ID NO 27
<211> LENGTH: 201
<212> TYPE: DNA
<213> ORGANISM: Glycine

<400> SEQUENCE: 27
aattaattac tcatagaact tgtaactat aaatattata ccaaccaact ttattcgtac     60
ctacccgtgt atatttatta tattttataa cttttttaagt taaaaaatac ttgtaacact  120
ttacaattaa aaattatatt tgttttttact attttcttcg ttcaagttac atttaattca  180
tttaatttaa ttaatatttta t                                            201

<210> SEQ ID NO 28
<211> LENGTH: 201
<212> TYPE: DNA
<213> ORGANISM: Glycine

<400> SEQUENCE: 28
attcatttaa tttaattaat atttattcat tcatttatttt attttttcatc attaatatttt  60 gacctaaaata tatttttaat tcctataaaa tgactaaatt ttgatttttga tgttttgttt   120 ttttcttctt ctttaatttg gttttcatct ccaaaaaagt gagataattg ttcataacaa   180
acagcagtcc tcttttttttt t                                             201

<210> SEQ ID NO 29
<211> LENGTH: 201
<212> TYPE: DNA
<213> ORGANISM: Glycine

<400> SEQUENCE: 29
aacaaacagc agtcctcttt tttttttaaca tatctttaaa tttcacctttt ttttataaaa  60 taacataaat tccatacata tttaataaaa tttatttcac tattacattg acattacagt   120
ttatgtaaaa aaaaatacac aaaaaaaagt aaaacagttt atgtatcttt gtaatgaaat   180
cttattaaat gtttgaatag a                                             201

<210> SEQ ID NO 30
<211> LENGTH: 201
<212> TYPE: DNA
<213> ORGANISM: Glycine

<400> SEQUENCE: 30
gaaatcttat taaatgtttg aatagatatt ttattttttta ttaaaaaatt atggttgaaa   60
gcttggatat cattaactca aaatataata atttatatta gatataacag atcgagatca   120
acctgataac gtgattcctc agtccaatat atattttttcc ggataaataa aggcccaatt   180
ggcaatggca tgtattacct t                                             201

<210> SEQ ID NO 31
<211> LENGTH: 201
<212> TYPE: DNA
<213> ORGANISM: Glycine

<400> SEQUENCE: 31
caattggcaa tggcatgtat taccttaatg caaccatgta ttactacttg catcagatag    60
agatagagta cgagccaata attgattaca tgcaaataca gccgcaaatt aacatcacga   120
```

```
acaattttaa ttaaatacct tcttttgtgc atataaataa ttaagatata tatagtggaa    180
gaaaaagacc acacagtgaa t                                              201

<210> SEQ ID NO 32
<211> LENGTH: 201
<212> TYPE: DNA
<213> ORGANISM: Glycine

<400> SEQUENCE: 32
tggaagaaaa agaccacaca gtgaatttgg gtaatctaaa ttaagatta ttttaaaata     60 aaaaggtaaa gtcataattt ttaattaaaa ttaataacaa aaatacgcat aaatatataa    120
aatatttaag tcattcaata ttattttca attaataatt ataattttta tgtttctaaa    180
atgcattcaa attcgatgga c                                              201

<210> SEQ ID NO 33
<211> LENGTH: 201
<212> TYPE: DNA
<213> ORGANISM: Glycine

<400> SEQUENCE: 33
ctaaaatgca ttcaaattcg atggacatct actttaattt caaacaaatt agtctaggaa    60
gatctttgtc gtaagtcatg attgaatttg caattttaac cgcaacaaat taaaaatttg   120
tcaagccaac atataacggt ggatatttaa gcacagaaag caagctggaa tggagacaac    180
aattttataa gatgatagtt g                                              201

<210> SEQ ID NO 34
<211> LENGTH: 201
<212> TYPE: DNA
<213> ORGANISM: Glycine

<400> SEQUENCE: 34
acaacaattt taagatga tagttgcaca ctttttttgct taaaaagtta tattgttata    60
tatataaaaa gttggtttga aaaaccacc atgtatgtgg aaaattgcgt acatatatca   120
atcttcgata acattcttct tacatatatc tgcatttaaa taggaaaaag gttaggtcca   180
ctacatctgc tcctaaccat a                                              201

<210> SEQ ID NO 35
<211> LENGTH: 201
<212> TYPE: DNA
<213> ORGANISM: Nicotiana

<400> SEQUENCE: 35
atgaagaatt tgattttcct aatgatgttt ctgatcatat tactacaaac aaacgccaat    60
aatctagtag aaactacatg caaaaacaca ccaaattatc aactttgtct gaaaactctg   120
ctttcggaca aacgaagtgc aacagggat attacaacgt tggcactaat tatggtcgat    180
gctataaaat ctaaggctaa t                                              201

<210> SEQ ID NO 36
<211> LENGTH: 201
<212> TYPE: DNA
<213> ORGANISM: Nicotiana

<400> SEQUENCE: 36
tcgatgctat aaaatctaag gctaatcaag ctgcactcac aatttcaaaa ctccggcatt    60
```

```
ctaatcctcc agcagcttgg aaaggtcctt tgaaaaattg tgcttttttca tataaggtaa    120 ttttaacagc aagtttgcct gaagcaattg aagctttaac aaaaggggat ccaaaatttg    180
ctgaagatgg aatggtaggt t                                               201
```

<210> SEQ ID NO 37
<211> LENGTH: 201
<212> TYPE: DNA
<213> ORGANISM: Nicotiana

<400> SEQUENCE: 37

```
atgaagaatt tgattttcct aacgatgttt ctgactatat tactacaaac aaacgccaat    60
aatctagtag aaactacatg caaaaacaca ccaaattacc aactttgtct gaaaactctg    120
ctttcggaca acgaagtgc aacaggggat atcacaacgt tggcactaat tatggtcgat    180
gcaataaaag ctaaagctaa t                                              201
```

<210> SEQ ID NO 38
<211> LENGTH: 201
<212> TYPE: DNA
<213> ORGANISM: Nicotiana

<400> SEQUENCE: 38

```
tcgatgcaat aaaagctaaa gctaatcagg ctgcagtgac aatttcgaaa ctccggcatt    60
cgaatccccc tgcagcttgg aaaggtcctt tgaaaaactg tgccttttca tataaggtaa    120
ttttaacagc aagtttgcct gaagcaattg aagcattgac aaaaggagat ccaaaatttg    180
ctgaagatgg aatggtaggt t                                              201
```

<210> SEQ ID NO 39
<211> LENGTH: 201
<212> TYPE: DNA
<213> ORGANISM: Nicotiana

<400> SEQUENCE: 39

```
atgagaaact tattccccat atttatgtta atcaccaatc tagcattcaa cgacaacaac    60
aacagtaata atatcatcaa cacgacctgc agagccacca caaactaccc cttgtgcctc    120
accaccctcc actctgatcc ccgtacctcc gaggccgagg gggcggacct caccaccctc    180
ggcctcgtca tggtagatgc g                                              201
```

<210> SEQ ID NO 40
<211> LENGTH: 201
<212> TYPE: DNA
<213> ORGANISM: Nicotiana

<400> SEQUENCE: 40

```
ccctcggcct cgtcatggta gatgcggtaa aattaaagtc catcgaaata atgaaaagta    60
taaaaaaact cgaaaaatcg aaccccgagt tgagactacc tcttagccaa tgttacatag    120
tgtattatgc tgttctacat gctgatgtaa ctgttgctgt tgaagcttta aaaagaggag    180
tccctaaatt tgctgaaaat g                                              201
```

<210> SEQ ID NO 41
<211> LENGTH: 201
<212> TYPE: DNA
<213> ORGANISM: Solanum

<400> SEQUENCE: 41

```
atgaaaattt tgattttcct aataatgttt cttgctatgt tgctagtaac aagtgggaat    60
```

```
aataatctag tagagacaac atgcaagaac acaccaaatt ataatttgtg tgtgaaaact    120
ttgtctttag acaaaagaag tgaaaaagca ggagatatta caacattagc attaattatg    180
gttgatgcta ttaaatctaa a                                              201
```

<210> SEQ ID NO 42
<211> LENGTH: 201
<212> TYPE: DNA
<213> ORGANISM: Solanum
<400> SEQUENCE: 42

```
ttatggttga tgctattaaa tctaaagcta atcaagctgc taatactatt tcaaaactta     60
ggcattctaa tcctcctcaa gcttggaaag atcctttgaa gaattgtgcc ttttcgtata    120
aggtaatttt accagcaagt atgccagaag cattagaagc attaacaaaa ggtgatccaa    180
aatttgcaga agatggaatg g                                              201
```

<210> SEQ ID NO 43
<211> LENGTH: 201
<212> TYPE: DNA
<213> ORGANISM: Solanum
<400> SEQUENCE: 43

```
taattatgat ctcaaattat taattctaat tacaacaata aatacatatc taataaaatt     60
taaaataaat ataaaattta aattaaaatt attaaatcgt aattaatact ctagctccag    120
aaaccaatca tgcaaatggt tccaaggaat caacccaaaa agaaagagat aagagaaagg    180
cataataaag tgatgcattc c                                              201
```

<210> SEQ ID NO 44
<211> LENGTH: 201
<212> TYPE: DNA
<213> ORGANISM: Solanum
<400> SEQUENCE: 44

```
aaaggcataa taaagtgatg cattccactt tcacaaggat aatgaaagga accattatct     60
ctaagaatta taaatgttaa ctacactaat aacattacaa ttgtaattat atttatatat    120
taaaatatac taattattat atacatttat cttttaggct atattatcat taaattaaaa    180
aatatattat aaatataaag t                                              201
```

<210> SEQ ID NO 45
<211> LENGTH: 201
<212> TYPE: DNA
<213> ORGANISM: Solanum
<400> SEQUENCE: 45

```
taaaaaatat attataaata taagttatt catttttttc tttttattata taaaatttat     60 ctgaaaattat atatacacat gcatcatttt ttttaaaaaa aattaattct acttaattca   120
ttttttaatt attaatatca tataactgtc caaaaattat tgctcatatg atgcctcaca   180
aatcatgctt tgtcttttc c                                              201
```

<210> SEQ ID NO 46
<211> LENGTH: 201
<212> TYPE: DNA
<213> ORGANISM: Solanum
<400> SEQUENCE: 46

```
tcacaaatca tgctttgtct ttttccaagt gtaaaaaggg aggtgcaata atgcattttg      60
gtttgtatac attttgtagt ttcaaagtct tatcatatta gaatcataga attaatgagt     120
agtatgattt aattatctaa ggcttgtttg gtagttagtt agaaactaaa tcattcaatt     180
gtattataaa tgatatgatt a                                               201

<210> SEQ ID NO 47
<211> LENGTH: 201
<212> TYPE: DNA
<213> ORGANISM: Solanum

<400> SEQUENCE: 47
caattgtatt ataaatgata tgattagcat tagagaggat aaaattatcc aataaaatta      60
cattttattt aagtttaaat taattatttta tctgtttatt tattaattta atttaattca    120
attcgattga ttttacaaat agccttaaaa agattgattt agaatttcga atctcgttta     180
acaaactcat taaataaatt g                                               201

<210> SEQ ID NO 48
<211> LENGTH: 201
<212> TYPE: DNA
<213> ORGANISM: Solanum

<400> SEQUENCE: 48
gtttaacaaa ctcattaaat aaattgcttc atctttaaaa aaattgttaa acataagtat      60
gaattgattt ttctacttat aaagcagatg ttcagaatat ttcaagataa taaacttatt    120
caattaatta taagttacgt aaaaaataaa atctaacgat aataaattaa ataatatttt    180
atttgaacat cggaatttat g                                               201

<210> SEQ ID NO 49
<211> LENGTH: 201
<212> TYPE: DNA
<213> ORGANISM: Solanum

<400> SEQUENCE: 49
attttatttg aacatcggaa tttatggtcg cgagcgaagc tagtaagcat ctcggaattc      60
tttctaaacc tcttcaaaa ttaaaatata tagtctcttc gatttcttca tatatgtacc    120
tcatgtttcg aatgaatttt aatgaaaatt ttaattctgt ccttcgaact gactactcta    180
gagactatct ccaggtccaa a                                               201

<210> SEQ ID NO 50
<211> LENGTH: 201
<212> TYPE: DNA
<213> ORGANISM: Solanum

<400> SEQUENCE: 50
ctctagagac tatctccagg tccaaacaaa cccacgaaaa acagattcaa cgaaaattct      60
gattccgtcc ctaaacctta ctaccctaga aactacaacc cccccccccc ccccaacaa    120 ggcccaaaca aaccccaccg aaaacacaaa gcaagagatg attaacacgc aattgaatcc    180
atccatttac tatataaaaa a                                               201

<210> SEQ ID NO 51
<211> LENGTH: 201
<212> TYPE: DNA
<213> ORGANISM: Vitis

<400> SEQUENCE: 51
```

-continued

```
atgagatcat ctgtgtttct cctgtgtgta atgggtcttt ctctgaccca aatcgaattc    60
tccacttcag atttggtaaa gcaaacatgc aagcatacac ccaactacga tctctgtgtg   120
aagactctgc tctcagaccc acgaagctct cacgcagacg tcgcaggttt ggccatggtg   180
atggtggacg tgatcaaggc c                                             201

<210> SEQ ID NO 52
<211> LENGTH: 201
<212> TYPE: DNA
<213> ORGANISM: Vitis

<400> SEQUENCE: 52
tggtgatggt ggacgtgatc aaggccaaaa caatcgccac cctccacaga atcagcgaat    60
tgctgggcac aacccgatac ccaaaaacga aggctgcctt gaggcgttgt gtagagttgt   120
atgataatgc agttttgaag gctgatcttc catcagcgat gcaagctctc aagactggtg   180
ttcccaaatt gcagaagaa g                                              201

<210> SEQ ID NO 53
<211> LENGTH: 21
<212> TYPE: DNA
<213> ORGANISM: Capsicum,N,Nicotiana

<400> SEQUENCE: 53
tggaatggta ggttcatctg g                                              21

<210> SEQ ID NO 54
<211> LENGTH: 21
<212> TYPE: DNA
<213> ORGANISM: Capsicum,N,Nicotiana

<400> SEQUENCE: 54
tgaacctacc attccatctt c                                              21

<210> SEQ ID NO 55
<211> LENGTH: 21
<212> TYPE: DNA
<213> ORGANISM: Capsicum,N,Nicotiana

<400> SEQUENCE: 55
gatggaatgg taggttcatc t                                              21

<210> SEQ ID NO 56
<211> LENGTH: 21
<212> TYPE: DNA
<213> ORGANISM: Capsicum,N,Nicotiana

<400> SEQUENCE: 56
gatgaaccta ccattccatc t                                              21

<210> SEQ ID NO 57
<211> LENGTH: 21
<212> TYPE: DNA
<213> ORGANISM: Capsicum,N,Nicotiana

<400> SEQUENCE: 57
gaagatggaa tggtaggttc a                                              21

<210> SEQ ID NO 58
<211> LENGTH: 21
<212> TYPE: DNA
```

<213> ORGANISM: Capsicum,N,Nicotiana

<400> SEQUENCE: 58
ccagatgaac ctaccattcc a                                         21

<210> SEQ ID NO 59
<211> LENGTH: 21
<212> TYPE: DNA
<213> ORGANISM: Capsicum,N,Nicotiana

<400> SEQUENCE: 59
cagatgaacc taccattcca t                                         21

<210> SEQ ID NO 60
<211> LENGTH: 21
<212> TYPE: DNA
<213> ORGANISM: Capsicum,N,Nicotiana

<400> SEQUENCE: 60
atggaatggt aggttcatct g                                         21

<210> SEQ ID NO 61
<211> LENGTH: 21
<212> TYPE: DNA
<213> ORGANISM: Capsicum,N,Nicotiana

<400> SEQUENCE: 61
atgaacctac cattccatct t                                         21

<210> SEQ ID NO 62
<211> LENGTH: 21
<212> TYPE: DNA
<213> ORGANISM: Capsicum,N,Nicotiana

<400> SEQUENCE: 62
agatggaatg gtaggttcat c                                         21

<210> SEQ ID NO 63
<211> LENGTH: 21
<212> TYPE: DNA
<213> ORGANISM: Capsicum,N,Nicotiana

<400> SEQUENCE: 63
agatgaacct accattccat c                                         21

<210> SEQ ID NO 64
<211> LENGTH: 21
<212> TYPE: DNA
<213> ORGANISM: Capsicum,N,Nicotiana

<400> SEQUENCE: 64
aagatggaat ggtaggttca t                                         21

<210> SEQ ID NO 65
<211> LENGTH: 250
<212> TYPE: DNA
<213> ORGANISM: Solanum lycopersicum

<400> SEQUENCE: 65
tcctttgaag aattgtgcct tttcgtataa ggtaatttta ccagcaagta tgccagaagc    60
attagaagca ttaacaaaag gtgatccaaa atttgcagaa gatggaatgg ttggttcttc   120
tggtgatgca caagaatgtg aagaatattt taaagctaca actattaaat attcaccact   180

```
ttctaaatta aatatagatg ttcatgaact ttctgatgtt ggtagagcca ttgtaagaaa    240
tttattgtaa                                                            250

<210> SEQ ID NO 66
<211> LENGTH: 46
<212> TYPE: DNA
<213> ORGANISM: Unknown
<220> FEATURE:
<223> OTHER INFORMATION: oligonucleotide primer containing T7 promoter
      sequence and complementary to 5' strand of SEQ ID NO 65

<400> SEQUENCE: 66
cagtctaata cgactcacta tagggagatc ctttgaagaa ttgtgc                    46

<210> SEQ ID NO 67
<211> LENGTH: 24
<212> TYPE: DNA
<213> ORGANISM: Unknown
<220> FEATURE:
<223> OTHER INFORMATION: oligonucleotide primer containing T7 promoter
      sequence and complementary to 3' strand of SEQ ID NO 65

<400> SEQUENCE: 67
ttacaataaa tttcttacaa tggc                                            24

<210> SEQ ID NO 68
<211> LENGTH: 184
<212> TYPE: DNA
<213> ORGANISM: Aequoria victoria

<400> SEQUENCE: 68
gatacccaga tcatatgaag cggcacgact tcttcaagag cgccatgcct gagggatacg     60
tgcaggagag gaccatctct ttcaaggacg acgggaacta caagacacgt gctgaagtca    120
agtttgaggg agacaccctc gtcaacagga tcgagcttaa gggaatcgat ttcaaggagg    180
acgg                                                                 184
```